(12) United States Patent
Mears et al.

(10) Patent No.: US 8,929,823 B2
(45) Date of Patent: Jan. 6, 2015

(54) HANDHELD DIABETES MANAGER WITH AUTOMATED DISCONNECT FEATURE

(71) Applicant: Roche Diagnostics Operations, Inc., Indianapolis, IN (US)

(72) Inventors: Mark G. Mears, Westfield, IN (US);
Mark Nierzwick, Brownsburg, IN (US);
Phillip E. Pash, Indianapolis, IN (US);
Vincent R. Rizzo, Indianapolis, IN (US);
Bettina Steiner, Kaiserstuhl (CH);
Kristin M. Westerfield, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 239 days.

(21) Appl. No.: 13/705,278

(22) Filed: Dec. 5, 2012

(65) Prior Publication Data
US 2013/0171938 A1    Jul. 4, 2013

Related U.S. Application Data

(60) Provisional application No. 61/581,149, filed on Dec. 29, 2011.

(51) Int. Cl.
*H04B 7/00* (2006.01)
*H04B 7/26* (2006.01)
*A61B 5/00* (2006.01)
*A61B 5/145* (2006.01)
*A61M 5/142* (2006.01)
*A61M 5/172* (2006.01)
*G06F 19/00* (2011.01)
*H04W 4/00* (2009.01)
*H04B 1/034* (2006.01)
*H04W 84/20* (2009.01)

(52) U.S. Cl.
CPC ............... *H04B 7/26* (2013.01); *A61B 5/7435* (2013.01); *A61B 5/0002* (2013.01); *A61B 5/14532* (2013.01); *A61M 5/14244* (2013.01); *A61M 5/1723* (2013.01); *G06F 19/3406* (2013.01); *G06F 19/3468* (2013.01); *H04W 4/001* (2013.01); *H04W 84/20* (2013.01); *A61M 2205/35* (2013.01); *A61M 2205/3569* (2013.01); *A61M 2205/3584* (2013.01)
USPC ........................................ 455/41.2; 455/100

(58) Field of Classification Search
CPC .................. A61M 2205/3576; H04B 7/26
USPC ................. 455/41.2, 41.3, 575.6, 90.1, 100
See application file for complete search history.

(56) References Cited

U.S. PATENT DOCUMENTS 7,912,655 B2    3/2011  Power et al.
7,976,467 B2    7/2011  Young et al.
(Continued)

OTHER PUBLICATIONS

Part 20601: Application Profile—Optimized Exchange Protocol, IEEE Std 11073-20601 Sep. 26, 2008.
(Continued)

*Primary Examiner* — Eugene Yun
(74) *Attorney, Agent, or Firm* — Harness, Dickey & Pierce, P.L.C.

(57) ABSTRACT

A computer-implemented method is provided for a handheld diabetes-management device to establish a data connection with a Continua manager. The method includes: receiving a request to establish a new data connection with a computing device, where the computing device is physically separated from the diabetes-management device and operates as a manager in accordance with IEEE standard 11073; determining whether the diabetes-management device has an existing data connection with a medical device that is physically separated from the diabetes-management device; terminating the existing data connection with the medical device in response to the determination that the diabetes-management device has an existing connection with the medical device; and establishing a new data connection with the computing device in accordance with IEEE standard 11073.

17 Claims, 32 Drawing Sheets

(56) References Cited

U.S. PATENT DOCUMENTS

| | | |
|---|---|---|
| 2009/0113295 A1 | 4/2009 | Halpern et al. |
| 2009/0305317 A1 | 12/2009 | Brauer et al. |
| 2010/0081911 A1 | 4/2010 | Sloan et al. |
| 2010/0105999 A1 | 4/2010 | Dixon et al. |
| 2010/0145164 A1* | 6/2010 | Howell .......................... 600/301 |
| 2010/0256047 A1 | 10/2010 | Sieh et al. |
| 2010/0317953 A1 | 12/2010 | Reggiardo et al. |
| 2010/0331654 A1 | 12/2010 | Jerdonek et al. |
| 2011/0178717 A1 | 7/2011 | Goodnow et al. |
| 2011/0193704 A1 | 8/2011 | Harper et al. |

OTHER PUBLICATIONS

Part 10417: Device Specilization—Glucose Meter, IEEE Std 11073-10417, May 8, 2009.

Continua Design Guidelines 2010, Oct. 1, 2010.

* cited by examiner

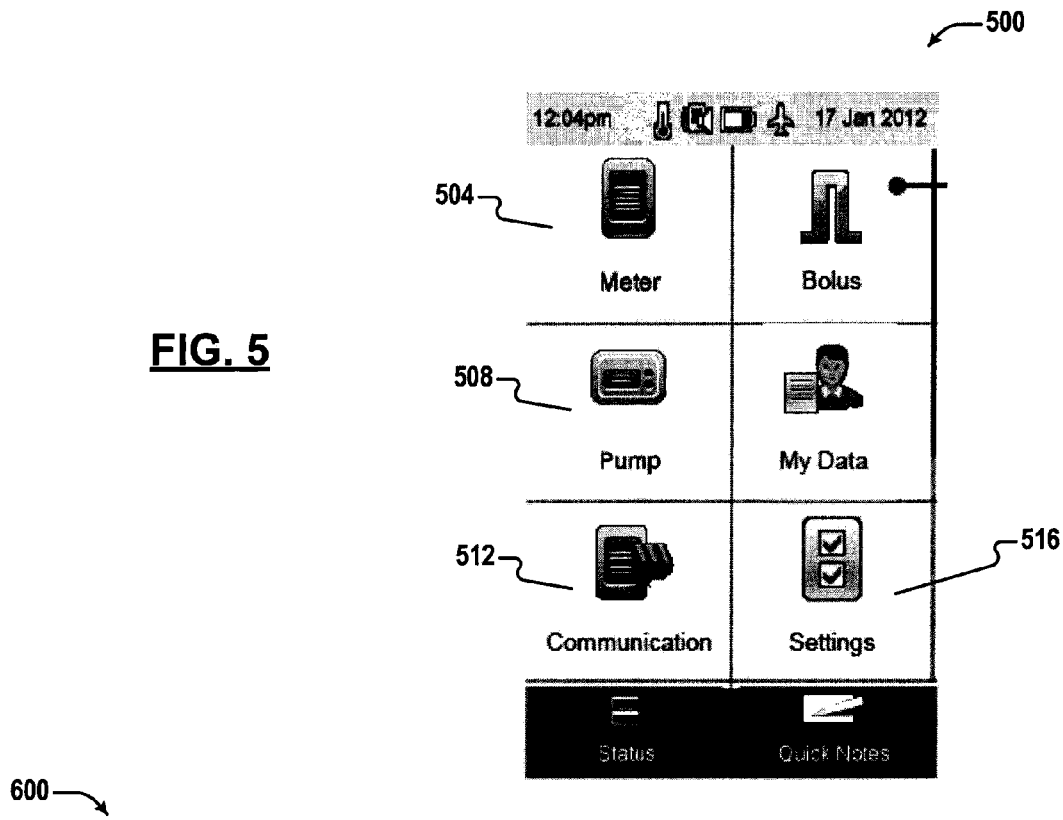
FIG. 5
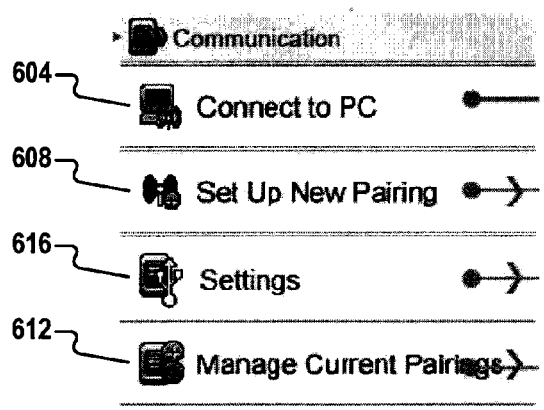
FIG. 6A

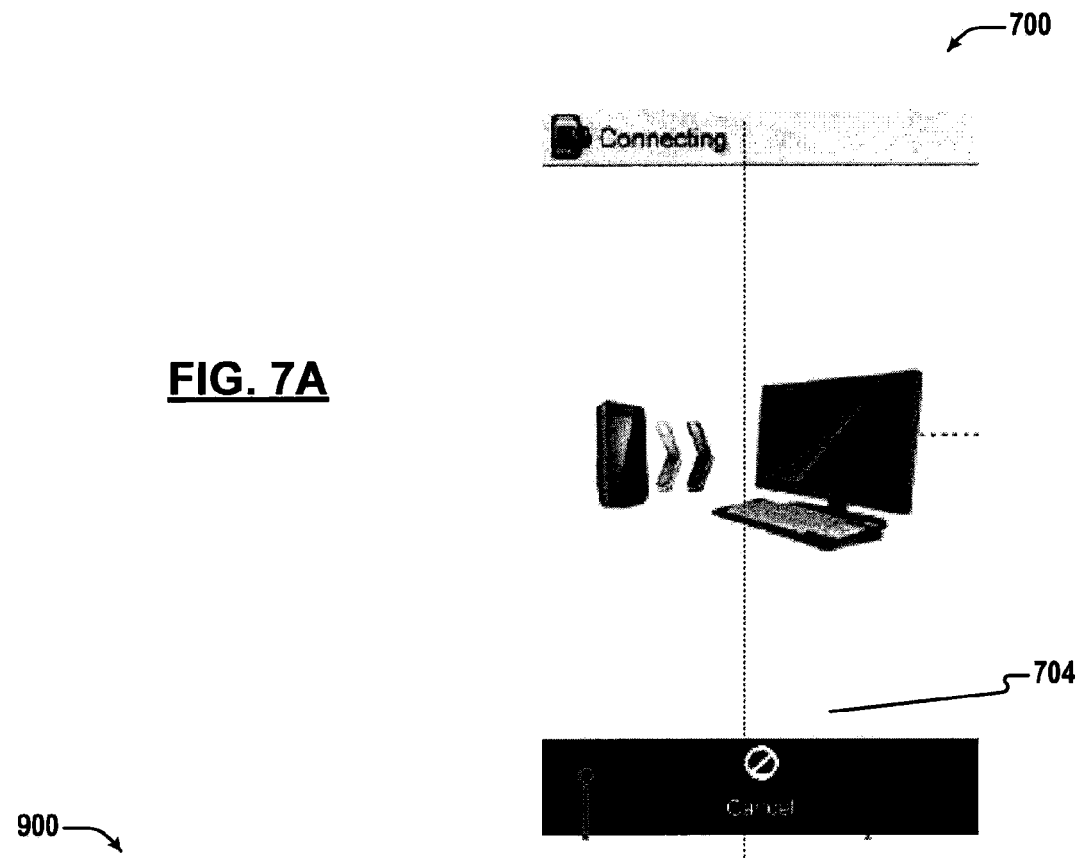
FIG. 7A
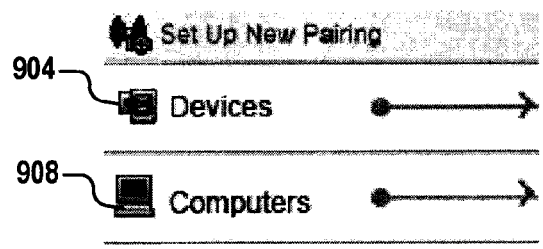
FIG. 9
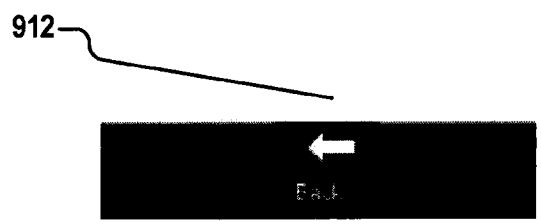

1000 ⟶

1004 ⟶

1050 ⟶

1058 ⟶ PUMP179926

1054 ⟶

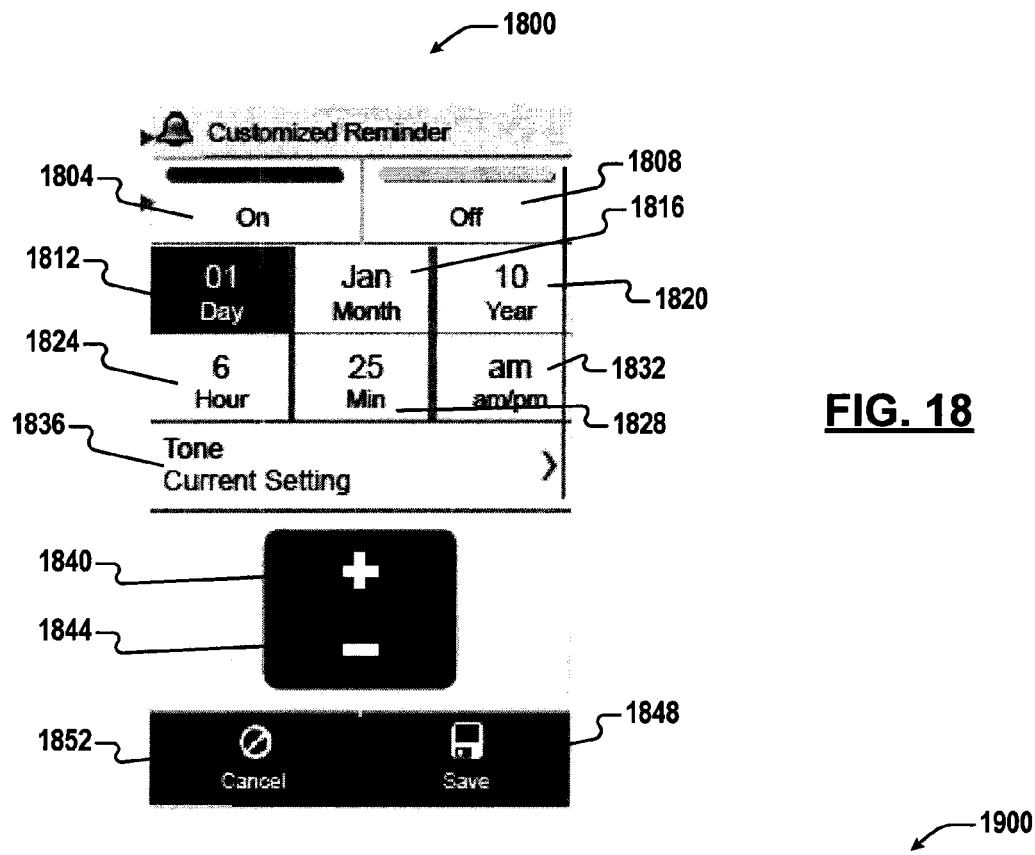
FIG. 18
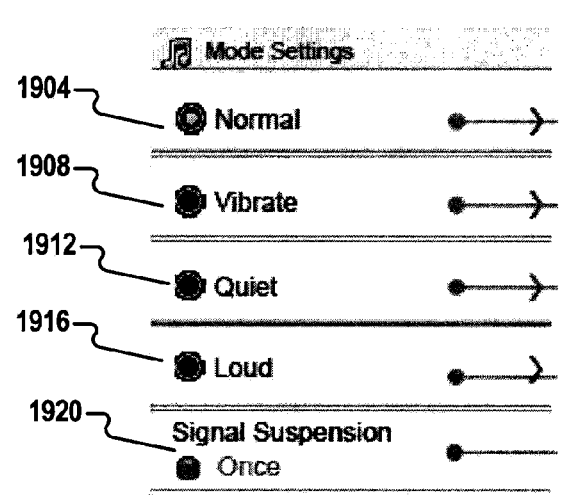
FIG. 19A

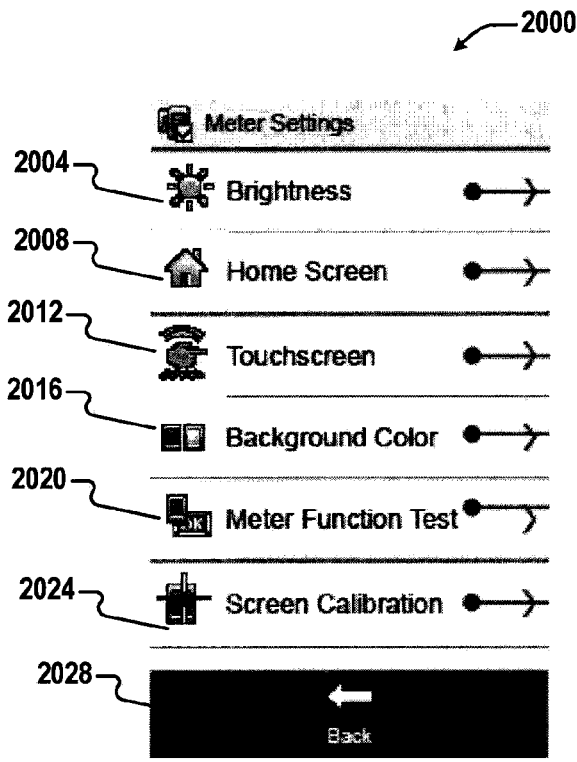
FIG. 20A
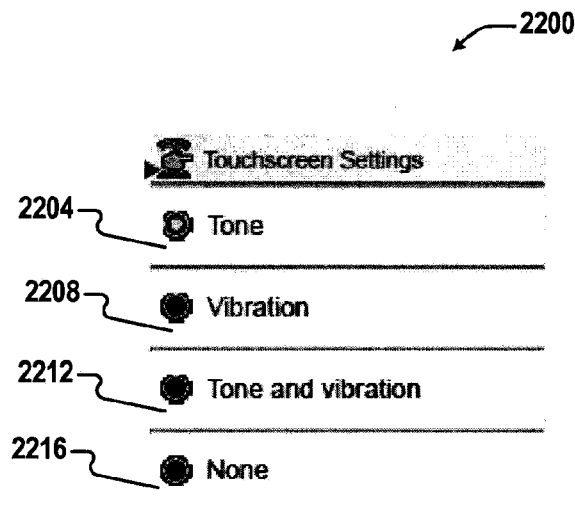
FIG. 22

HANDHELD DIABETES MANAGER WITH AUTOMATED DISCONNECT FEATURE

CROSS-REFERENCE TO RELATED APPLICATIONS

This application claims the benefit of U.S. Provisional Application No. 61/581,149, filed on Dec. 29, 2011. The disclosure of the above application is incorporated herein by reference in its entirety.

FIELD

The present disclosure relates to a handheld diabetes manager having an automated-disconnect feature particularly suited for devices communicating in accordance with IEEE standard 11073.

BACKGROUND

According to the American Diabetes Association, diabetes mellitus, or simply, diabetes, is a group of diseases characterized by high blood glucose levels that result from defects in the body's ability to produce and/or use insulin. Type 1 diabetes is usually diagnosed in children and young adults, and was previously known as juvenile diabetes. In type 1 diabetes, the body does not produce insulin. Type 2 diabetes is the most common form of diabetes. In type 2 diabetes, either the body does not produce enough insulin or the cells ignore the insulin. During pregnancy—usually around the $24^{th}$ week—many women develop gestational diabetes. A diagnosis of gestational diabetes doesn't mean that you had diabetes before you conceived, or that you will have diabetes after giving birth.

Diabetes is managed primarily by controlling the level of glucose in the bloodstream. This level is dynamic and complex, and it is affected by multiple factors including the amount and type of food consumed and the amount of insulin (which mediates transport of glucose across cell membranes) in the blood. BG levels are also sensitive to exercise, sleep, stress, smoking, travel, illness, menses, and other psychological and lifestyle factors unique to individual patients. The dynamic nature of BG, insulin, and all other factors affecting BG often require a person with diabetes to forecast BG levels. Therefore, therapy in the form of insulin, oral medications, or both, can be timed to maintain BG levels in an appropriate range.

Management of diabetes is time-consuming for patients because of the need to consistently obtain reliable diagnostic information, follow prescribed therapy, and manage lifestyle on a daily basis. Diagnostic information, such as BG level, is typically measured with a handheld BG meter using a capillary blood sample obtained with a lancing device. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting of meal composition (fats, carbohydrates, and proteins) and the effects of exercise or other physiological states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient-recorded logs, from laboratory tests, and from healthcare-professional recommendations. Medical devices include patient-owned BG meters, continuous glucose monitors, ambulatory insulin-infusion pumps, diabetes-analysis software, and diabetes-device configuration software. Each of these systems generates and/or manages large amounts of diagnostic and prescriptive data. Personal healthcare devices include weight scales, blood-pressure cuffs, exercise machines, thermometers, and weight-management software. Patient-recorded logs include information relating to meals, exercise, and lifestyle. Lab test results include HbA1C, cholesterol, triglycerides, and glucose tolerance. Healthcare-professional recommendations include prescriptions, diets, test plans, therapy changes and other information relating to the patient's treatment.

Patients with diabetes and their healthcare professionals interact with a variety of medical devices and systems to help manage the disease. For each of these differing types of medical devices, there is a need to aggregate, manipulate, manage, present, and communicate diagnostic data and prescriptive data from multiple data sources in an efficient manner to improve the care and health of a person with diabetes, so the person with diabetes can lead a full life and reduce the risk of complications from diabetes. There is also a need to aggregate, manipulate, manage, present, and communicate such diagnostic data and prescriptive data amongst the different types of medical devices using a standard communication protocol. Continua® Health Alliance ("Continua") is a trade association working toward establishing such a protocol via systems and standards for interoperable medical devices. Design guidelines put forth by Continua leverage various IEEE standards, including IEEE 11073, which pertains to the interoperability of personal healthcare devices. Safety is of concern when different health devices interact with one another because unexpected interfacing problems can occur. Standard protocols lead to predictable outcomes and make it possible for patients to rely on such a diabetes manager.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

This section provides a general summary of the disclosure, and is not a comprehensive disclosure of its full scope or all of its features.

A computer-implemented method is provided for a handheld diabetes-management device to establish a data connection with a Continua manager. The method include: receiving by a diabetes-management device a request to establish a new data connection with a computing device, where the computing device is physically separated from the diabetes-management device and operates as a manager in accordance with IEEE standard 11073; determining whether the diabetes-management device has an existing data connection with a medical device that is physically separated from the diabetes-management device; terminating the existing data connection with the medical device in response to the determination that the diabetes-management device has an existing connection with the medical device; and establishing a new data connection with the computing device in accordance with IEEE standard 11073.

In another aspect of the disclosure, the handheld diabetes-management device provides an automated disconnect feature when establishing a data connection with a Continua manager. The diabetes-management device generally includes: a port configured to receive a test strip for blood glucose measurement; a blood glucose measurement module cooperatively operable with a test strip inserted in the port for blood glucose measurement; and a communications module that selectively communicates via a wireless data link with a medical device, the medical device being physically separated from the diabetes manager. In addition, a connectivity module is configured to receive a request to establish a new data connection with a computing device and operates, in response to the request, to determine whether the diabetes-management device has an existing data connection with the medical device. The connectivity module further operates, in response to the determination that the diabetes-management device has an existing data connection with the medical device, to terminate the existing data connection with the medical device, where the computing device is physically separated from the diabetes-management device and operates as a manager in accordance with IEEE standard 11073.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The drawings described herein are for illustrative purposes only of selected embodiments and not all possible implementations, and are not intended to limit the scope of the present disclosure. The present disclosure will become more fully understood from the detailed description and the accompanying drawings, wherein:

FIG. 5 is an exemplary home screen of a diabetes manager according to the present teachings;

FIG. 6A is an exemplary communication screen of a diabetes manager according to the present teachings;

FIG. 7A is an exemplary connecting screen of a diabetes manager according to the present teachings;

FIG. 9 is an exemplary set-up-new-pairing screen of a diabetes manager according to the present teachings;

FIG. 18 is an exemplary custom screen of a diabetes manager according to the present teachings;

FIG. 19A is an exemplary mode-settings screen of a diabetes manager according to the present teachings;

FIG. 20A is an exemplary meter-settings screen of a diabetes manager according to the present teachings;

FIG. 22 is an exemplary touchscreen-settings screen of a diabetes manager according to the present teachings;

Corresponding reference numerals indicate corresponding parts throughout the several views of the drawings.

DETAILED DESCRIPTION

Figure 1:
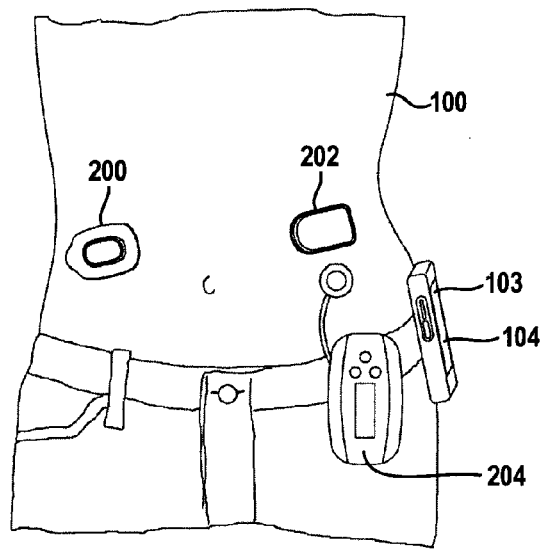
FIG. 1 shows a patient with a continuous glucose monitoring (CGM) patch, an ambulatory durable insulin infusion pump, an ambulatory non-durable insulin infusion pump, and a diabetes manager.

Referring now to FIG. 1, a person with diabetes using various medical devices is illustrated. Persons with diabetes include persons with metabolic syndrome, persons with pre-diabetes, type 1 diabetics, type 2 diabetics, and gestational diabetics, and they are collectively referred to as a patient 100. Healthcare providers for diabetes are diverse and include nurses, nurse practitioners, physicians, diabetes nurse educators, nutritionists and endocrinologists, and they are collectively referred to as a clinician.

During a healthcare consultation, the patient 100 typically shares a variety of patient data with the clinician, including BG measurements, continuous glucose monitor data, amounts of insulin infused, amounts of foods and beverages consumed, exercise schedules, and other lifestyle information. The clinician may obtain additional patient data that includes measurements of HbA1C, cholesterol levels, triglycerides, blood pressure, and weight of the patient 100. The patient data can be recorded manually or electronically on a handheld diabetes-management device 104 having a display 103, a diabetes analysis software executed on a personal computer (PC) 106, and/or a web-based diabetes analysis site (not shown). The clinician can analyze the patient data manually or electronically using the diabetes analysis software and/or the web-based diabetes analysis site. After analyzing the patient data and reviewing adherence of the patient 100 to previously prescribed therapy, the clinician can decide whether to modify the therapy for the patient 100.

Referring still to FIG. 1, the patient 100 can use a continuous glucose-monitoring (CGM) device 200, an ambulatory non-durable-insulin-infusion pump 202, or an ambulatory durable-insulin-infusion pump 204 (hereafter "insulin pump" or "pump" 202 or 204), and the handheld diabetes-management device 104 (hereafter the diabetes manager 104). The CGM Device 200 includes a body mount, a reusable component, and a subcutaneous sensor to sense and monitor the amount of glucose in interstitial fluid of the patient 100. The CGM Device 200 communicates corresponding data to the diabetes manager 104.

The diabetes manager 104 can perform various tasks, including measuring and recording BG levels; determining an amount of insulin to be administered to the patient 100 via the insulin pump 202 or 204; receiving patient data via user interface; archiving the patient data; etc. The diabetes manager 104 periodically receives data from the CGM Device 200 from which glucose levels of the patient 100 are computed. The diabetes manager 104 transmits instructions to the insulin pump 202 or 204, which delivers insulin to the patient 100. Insulin can be delivered in a scheduled manner in the form of a basal dose, which maintains a predetermined insulin dose to the patient 100. Additionally, insulin can be delivered in the form of a bolus dose, which raises the amount of insulin delivered to the patient 100 by a determined amount.

Figure 2:
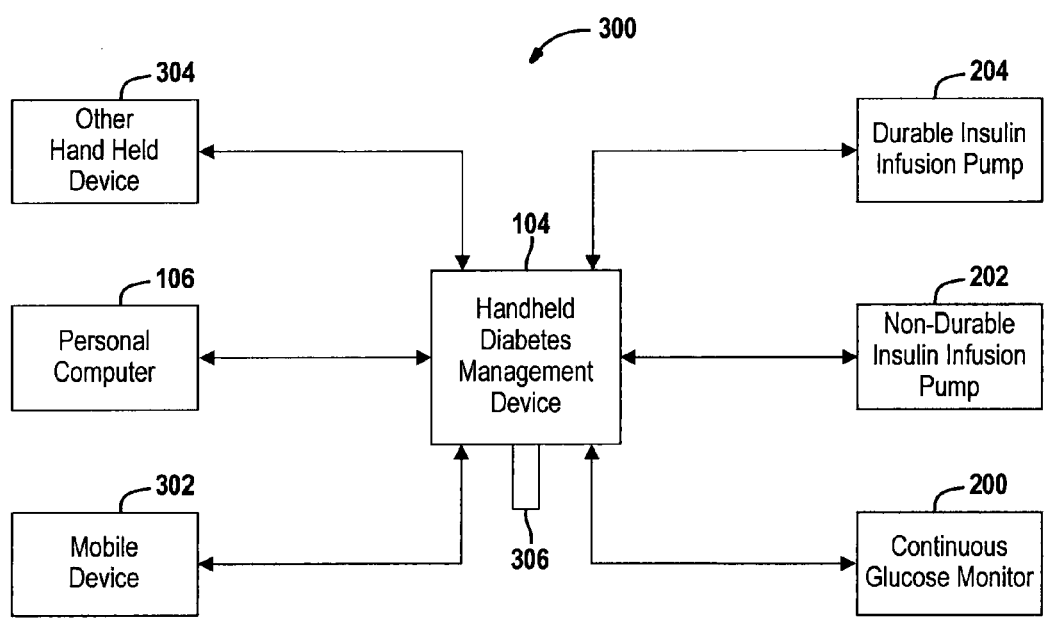
FIG. 2 shows a diabetes-management system used by patients and clinicians to manage diabetes.

Generally, and referring now to FIG. 2, a diabetes-management system 300 used by the patient 100 and the clinician may include one or more of the following devices: the diabetes manager 104, the continuous glucose monitor (CGM Device) 200, the insulin pump 202 or 204, a mobile device 302, the PC 106 with diabetes-analysis software, and other healthcare devices 304. The diabetes manager 104 can be configured as a system hub that communicates with the devices of the diabetes-management system 300. Alternatively, the mobile device 302 can serve as the system hub. Communication between the devices in the diabetes-management system 300 can be performed using wireless interfaces (e.g., Bluetooth) and/or wired interfaces (e.g., USB). Communication protocols used by these devices may include protocols compliant with the IEEE 11073 standard, as extended using guidelines provided by Continua® Health Alliance Design Guidelines. Further, healthcare records systems can be used by the patient 100 and the clinician to exchange information.

In an exemplary embodiment, communication between the devices occurs in accordance with IEEE standard 11073. The communication model employs the concept of "managers" and "agents." Agents are generally smaller personal health devices that lack processing power; whereas, managers are more powerful computing devices such as a smart phone or desktop computer. To communicate, an agent initiates an association between itself and a manager. The agent issues an association request and the manager responds with an acceptance of the association request. In this way, the agent and manager form an association and enter into an operating state. In the context of FIG. 2, the diabetes manager 104 acts as an "agent" in relation to the PC 106 or the mobile device 302, which act as "managers". That is, the diabetes manager 104 may initiate an association between itself and the PC 106 or the mobile device 302. In some embodiments, the diabetes manager 104 may communicate with the insulin pumps 202 or 204, the CGM Device 200, and the other healthcare devices 304 using a communication protocol other than IEEE11073. In other embodiments, the diabetes manager 104 may communicate with these other devices as a "manager" in accordance with IEEE 11073. In other words, the diabetes manager 104 operates as both a "manager" and an "agent" depending on whom it is communicating with.

The diabetes manager 104 can receive glucose readings from one or more sources (e.g., from the CGM Device 200). The CGM Device 200 regularly monitors the interstitial glucose level of the patient 100. The CGM Device 200 periodically communicates data to the diabetes manager 104. The diabetes manager 104 computes glucose levels of the patient based on this data. The diabetes manager 104 and the CGM Device 200 communicate wirelessly, generally using a proprietary wireless protocol such as, for example, the Gazell wireless protocol developed by Nordic Semiconductor, Inc., Sunnyvale, Calif. Any other suitable wireless protocol may be used instead.

Additionally, the diabetes manager 104 includes a BG meter (BGM) and a port that communicates with the BGM (not shown). The port can receive a BG-measurement strip 306. The patient 100 deposits a sample of blood on the BG-measurement strip 306. The BGM analyzes the sample and measures the BG level in the sample. The BG level measured from the sample and/or the glucose level computed using data received from the CGM Device 200 can be used to determine the amount of insulin to be administered to the patient 100.

The diabetes manager 104 can also communicate with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information, including meal and/or exercise schedules of the patient 100. In some embodiments, the insulin pump 202 or 204 can determine the amount of insulin to administer to the patient 100 based on the additional information. In another embodiment, the diabetes manager can determine the amount of insulin to administer to the patient.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication transport such as Bluetooth. Other wireless or wired communication transports can also be used.

In addition, the diabetes manager 104 can communicate with the other healthcare devices 304. For example, the other healthcare devices 304 may include a blood pressure meter, a weight scale, a pedometer, a fingertip-pulse oximeter, a thermometer, etc. The other healthcare devices 304 obtain and communicate personal health information of the patient 100 to the diabetes manager 104 through wireless, USB, or other interfaces. The other healthcare devices 304 may use communication protocols compliant with ISO/IEEE 11073 extended using guidelines from Continua® Health Alliance. The diabetes manager 104 can communicate with the other healthcare devices 304 using interfaces including Bluetooth, USB, etc. Further, the devices of the diabetes-management system 300 can communicate with each other via the diabetes manager 104.

The diabetes manager 104 can communicate with the PC 106 using Bluetooth, USB, or other interfaces. A diabetes-management software running on the PC 106 includes an analyzer-configurator that stores configuration information of the devices of the diabetes-management system 300. The configurator has a database to store configuration information of the diabetes manager 104 and the other devices. The configurator can communicate with users through standard web or computer screens in non-web applications. The configurator transmits user-approved configurations to the devices of the diabetes-management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth or other suitable wireless communication transport. The mobile device 302 may include a cellular phone, a pager, or a personal digital assistant (PDA). The diabetes manager 104 can send messages to an external network through the mobile device 302. The mobile device 302 can transmit messages to the external network upon receiving requests from the diabetes manager 104.

If the diabetes manager 104 is connected to a medical device such as the insulin pump 202 or 204 or the CGM device 200, the diabetes manager 104 disconnects from the medical device prior to establishing a connection to a computing device such as the PC 106, the mobile device 302, or the other healthcare device 304.

Figure 3:
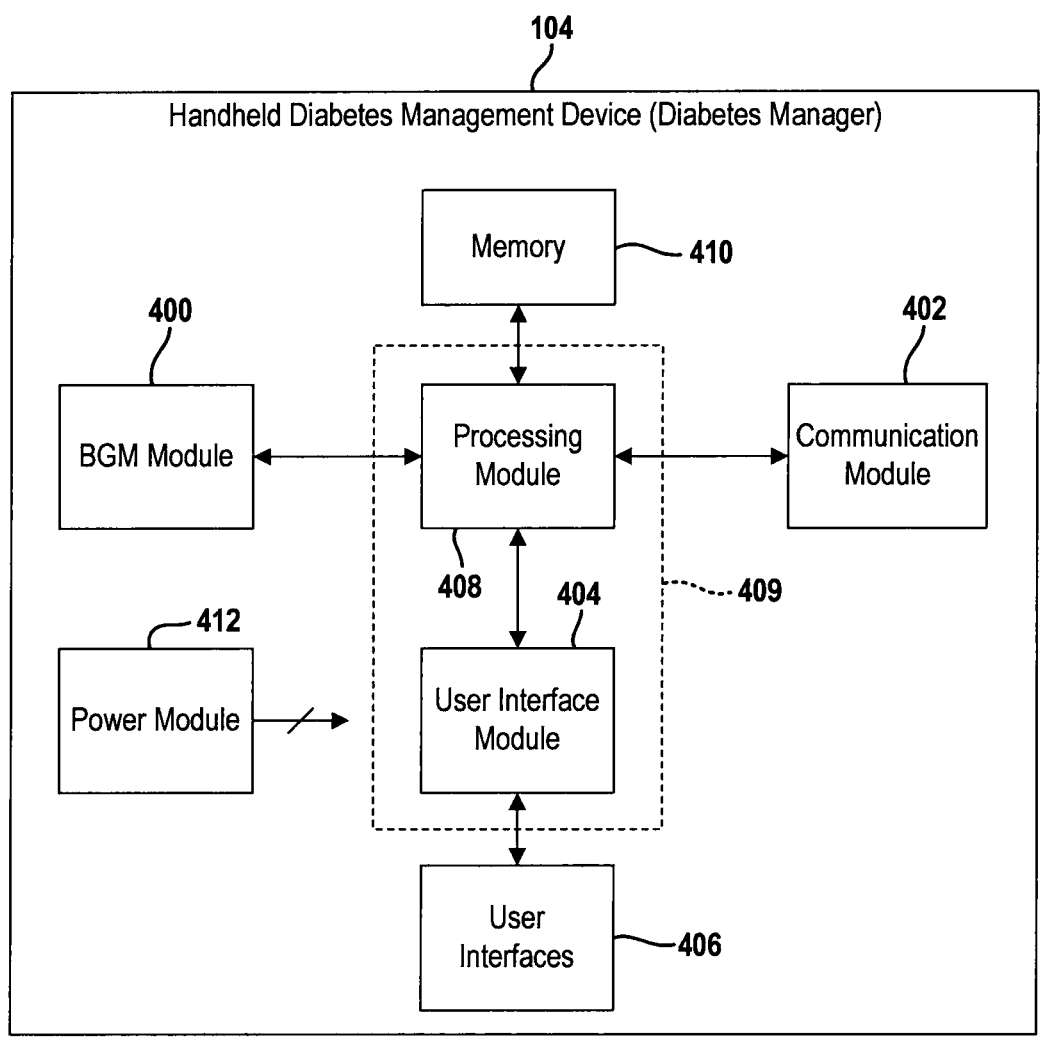
FIG. 3 is a functional block diagram of a diabetes manager according to the present teachings.

Referring now to FIG. 3, the diabetes manager 104 comprises a BG-measurement module 400, a communication module 402, a UI module 404, user interfaces 406, a processing module 408, a memory 410, and a power module 412. The UI module 404 and the processing module 408 can be implemented by an application-processing module 409. The BG-measurement module 400 includes a BG-measuring engine that analyzes samples provided by the patient 100 on the BG-measurement strip 306 and that measures the amount of BG in the samples. The communication module 402 includes multiple radios that communicate with different devices of the diabetes-management system 300. The UI module 404 interfaces the diabetes manager 104 with various user interfaces 406 that the patient 100 can use to interact with the diabetes manager 104. For example, the user interfaces 406 can include a touchscreen display or other suitable display, touchscreen keys or other suitable keys, switches, a display, a speaker, a microphone, a secure digital (SD) card port, a USB port, etc. (not shown).

The processing module 408 processes data received from the BG-measurement module 400, the communication module 402, and the UI module 404. The processing module 408 uses the memory 410 for processing and storing data. The memory 410 can include volatile and nonvolatile memory. The processing module 408 outputs data to and receives data from the user interfaces 406 via the UI module 404. The processing module 408 outputs data to and receives data from the devices of the diabetes-management system 300 via the communication module 402. The power module 412 supplies power to the components of the diabetes manager 104. The power module 412 can include a rechargeable battery. The battery can be recharged using an adapter that plugs into a wall outlet. The battery can also be charged via the USB port of the diabetes manager 104.

Figure 4:
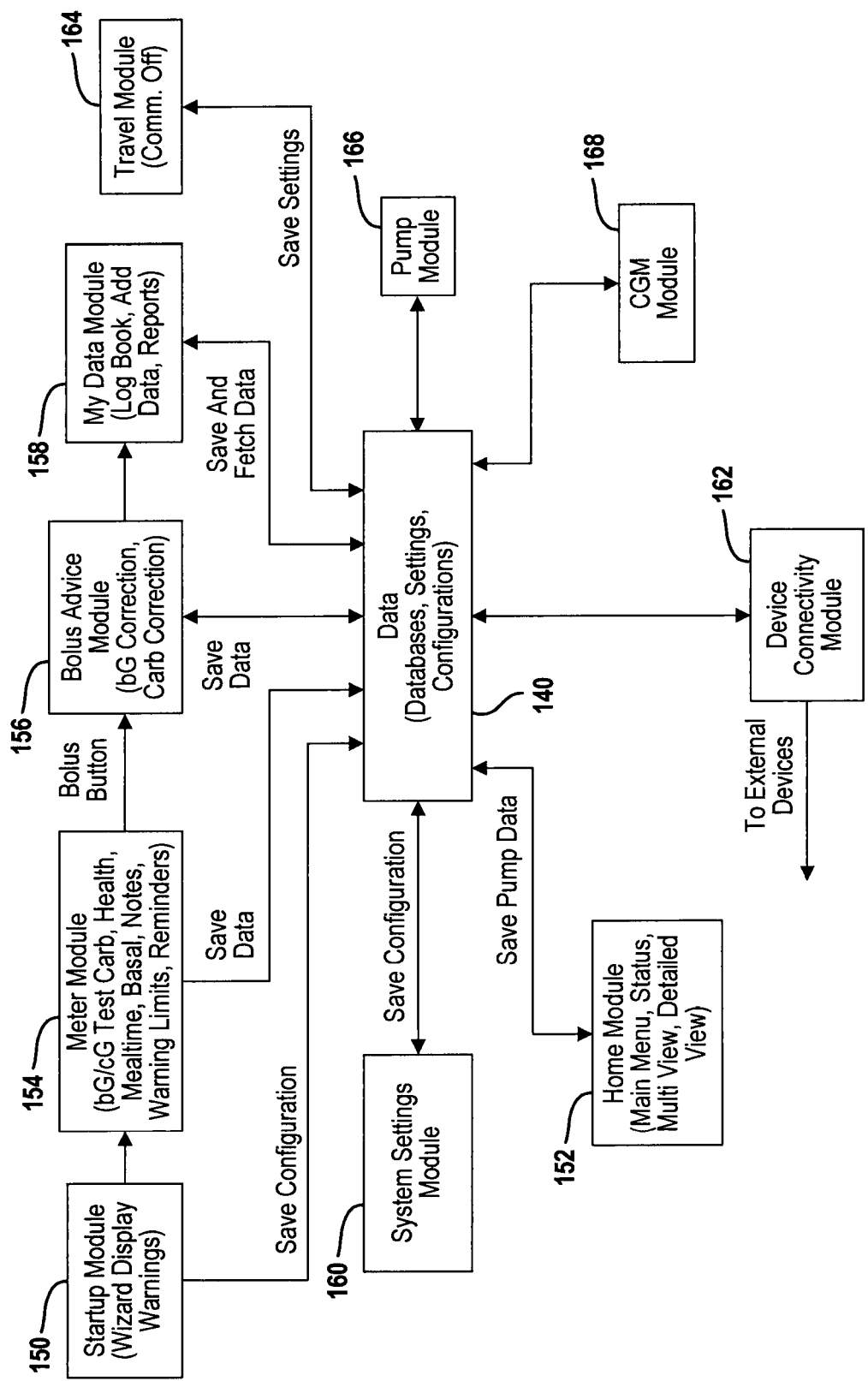
FIG. 4 is a block diagram illustrating a UI with a device-connectivity module for a diabetes manager according to the present teachings.

Referring to FIG. 4, a logical screen-navigation architecture of the UI module 404 for the diabetes manager 104 is illustrated. The following modules can be integrated in the navigation architecture of the diabetes manager 104: a startup module 150, a home module 152, a UI meter module 154, a bolus advice module 156, a "my data" module 158, a system-settings module 160, a device-connectivity module 162, a travel module 164, a UI pump module 166 and a data module 140. The data module 140 includes databases, settings, and configurations. The data module 140 acts as a central hub that communicates with the other modules to store and provide information regarding data, settings, and configurations related to the other modules. In some embodiments, some of the modules can be removed or inactivated, or additional modules can be added. For example, the UI pump module 166 may be removed or inactivated in models of the diabetes manager 104 for non-pump users. In other embodiments, a continuous glucose monitoring (CGM) module 168 can be added.

As briefly outlined in reference to FIG. 4, the diabetes manager 104 of the present teachings integrates various functions, controls, calculations, tests, and reports in a single handheld device. In prior art devices, these various functions, controls, calculations, tests, and reports are typically split among different specialized devices such as single-purpose BG meters, single-purpose remote devices for insulin pumps, and other similar single or limited-purpose diabetes managers. Integrating the multiple tasks and functions of the plurality of modules of the diabetes manager 104 of the present teachings requires a UI that does not simply superimpose various functions in an additive manner. The UI design anticipates use case scenarios that are unique and emerge from the interactions of the multiplicity of modules when all these modules are integrated in the same handheld device. Such interactions arise not just from the hardware aspects of the device, but from the various possibilities or use scenarios that a user may subject the device to be based on the user-perceived and/or actual capabilities of the device. For example, although portability is common to many prior art diabetes devices, portability and use in restricted or semi-restricted environments, such as during air travel, requires anticipation of alternative use cases or use scenarios to avoid conflicts without totally disabling the device. In the content of this disclosure, the term "pump" is used interchangeably with the term "insulin pump," and the term "insulin patch" is used interchangeably with the term "CGM device," unless differentiation is required.

In the context of the UI for the diabetes manager 104, a use case is an observable result based upon an action by a user. A use case describes the behavior and navigation along a primary or alternate path including any standard business rules for diabetes-management and is graphically represented in an activity or behavior diagram, as shown for example in FIGS. 6B, 7B, 10B, 10C, 11A and 11B, 12B, and 13B.

Referring to FIG. 5, an exemplary home screen 500 of the diabetes manager 104 is illustrated. The home screen 500 includes various buttons (mechanical or touch buttons) that can be activated by touch or stylus or other selector device to display a corresponding detailed screen. The home screen 500 is generally device-centric, i.e., it is organized and centered around connected or connectable devices according to a predetermined or preselected hierarchy rather than functions or capabilities of the diabetes manager 104. The connected or connectable devices in the hierarchy of the UI can include internal and external devices. An internal device can be, for example, a BGM or "meter" associated with the UI meter module 154 (FIG. 4) and the BG-measurement module 400 (FIG. 3). External devices can include a pump, such as insulin pumps 202 or 204, a CGM Device 200, and/or other devices described above in connection with FIG. 2.

In FIG. 5, a meter button 504 represents the UI meter module 154 and interfaces with the internal device for the BG-measurement module 400. A pump button 508 illustrates the UI for an external device, in this case a pump, as shown in the UI pump module 166 (FIG. 4) and in FIGS. 2 at 202 and 204. Another button corresponding to the UI for a CGM module 168 (FIG. 4) and at 200 in FIG. 2 can be added, as well as buttons for additional external devices. The pump button 508 is used to represent any such external devices, with the insulin-infusion pumps 202 or 204 and the CGM Device 200 being exemplary devices. The home screen 500 may include a communication button 512 corresponding to the device-connectivity module 162 of the UI module 404. The home screen 500 may include a settings button 516 corresponding to the system-settings module 160 of the UI module 404. Pressing (or touching) any of the buttons in the home screen 500 leads to a more detailed screen for the function of the button that was pressed.

Referring now to FIG. 6A, an exemplary communication screen 600 of the diabetes manager 104 is illustrated. Pressing (or touching) the communication button 512 of the home screen 500 displays the communication screen 600. The communication screen 600 may include various buttons (mechanical or touch buttons) that can be activated by touch or stylus or other selector device to display a corresponding detailed screen. The communication screen 600 may include a connect-to-PC button 604, a set-up-new-pairing button 608, a manage-current-pairings button 612, a settings button 616, and a back button 620. Pressing the back button 620 displays the home screen 500.

Figure 6B:
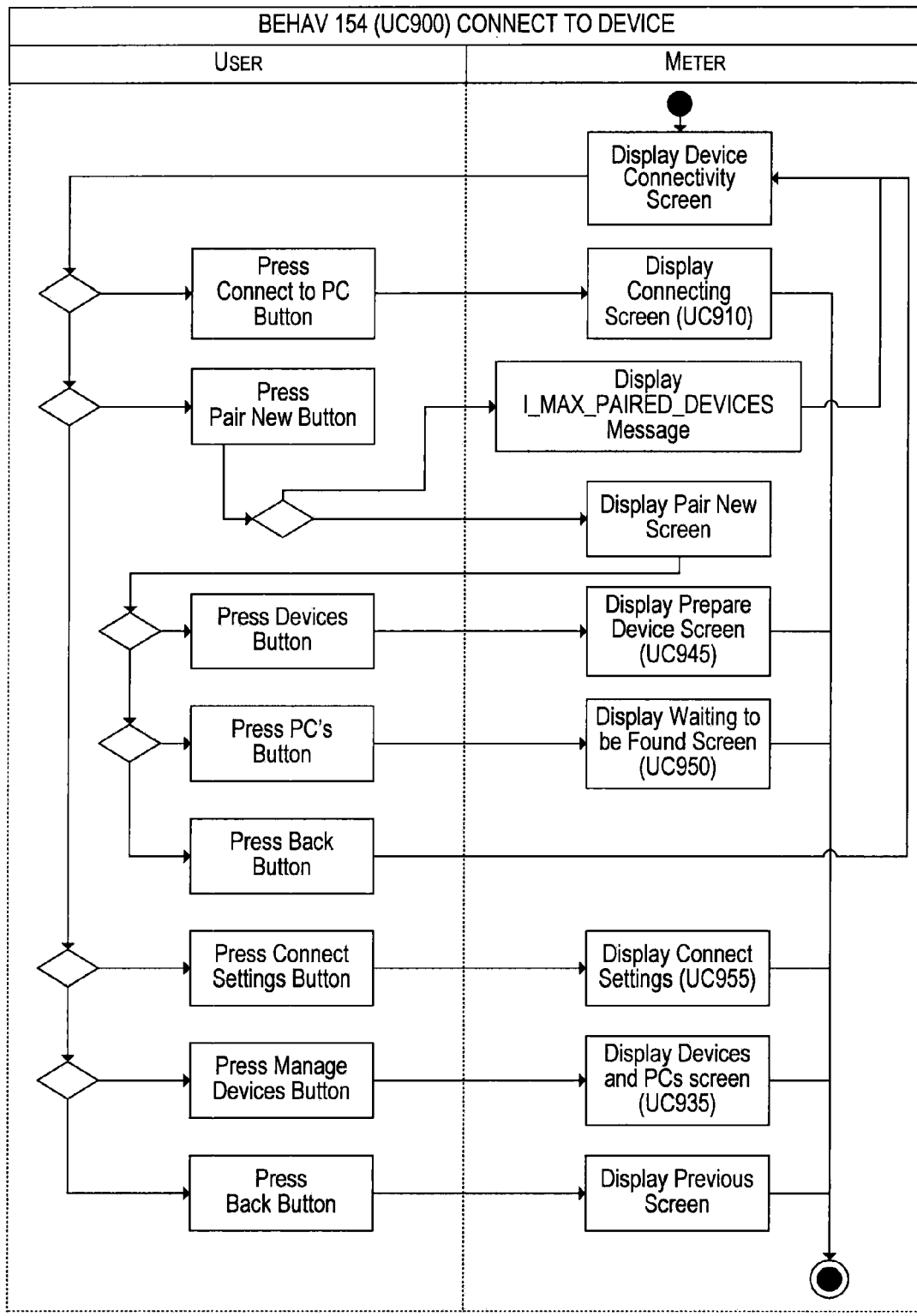
FIG. 6B is an activity diagram illustrating behavioral flow for connecting a diabetes manager to a device, pairing the diabetes manager with a device, modifying connection settings, and managing paired devices according to the present teachings.

FIG. 6B serves as a use case map of the device-connectivity module 162, illustrating the behavioral flow for connecting a diabetes manager to a device and managing that connection. The behavioral flows for connecting to a computing device, setting up a new pairing with a device, managing current pairings, and configuring connection settings are illustrated.

FIG. 7A illustrates an exemplary connecting screen 700 of the diabetes manager 104. The connecting screen 700 may include various buttons (mechanical or touch buttons) that can be activated by touch or stylus or other selector device to display a corresponding screen. The connecting screen 700 may display an animation while the diabetes manager 104 is attempting to connect a device, for example, PC 106. The connecting screen 700 may include a cancel button 704.

With reference to FIGS. 6A, 6B, and 7A, the user may attempt to connect to another computing device, for example PC 106, by pressing (or touching) the connect-to-PC button 604 of the communication screen 600. When the connect-to-PC button 604 is pressed and an active USB cable is attached, the diabetes manager 104 shall display the connecting screen 700 while making a USB connection with the device connected to the other end of the USB cable. When the connect-to-PC button 604 is pressed and no active USB cable is attached, the diabetes manager 104 shall display the connecting screen 700 while making itself connectable to another wireless device. Similarly, when the connect-to-PC button 604 is pressed with no active USB cable attached and the diabetes manager 104 is paired with another device, the diabetes manager 104 shall display the connecting screen 700 while making itself connectable to another wireless device. Of note, if the connect-to-PC button 604 is pressed, and the diabetes manager 104 is connected to another device, such as the insulin pump 202 or 204, the diabetes manager 104 will disconnect from the other device prior to connecting to the PC 106 as further described below in relation to FIG. 8.

On the other hand, when the connect-to-PC button 604 is pressed while no active USB cable is attached, and the diabetes manager 104 is not paired with another device, the diabetes manager 104 shall display an invalid-connection message. Likewise, when the connect-to-PC button 604 is pressed while an active charging cable is attached, but the diabetes manager 104 is not paired to another device, the diabetes manager 104 shall display the invalid-connection message. Once the invalid-connection message is acknowledged, for example, by pressing an okay button of the invalid-connection message, the diabetes manager 104 displays the communication screen 600.

Figure 7B:
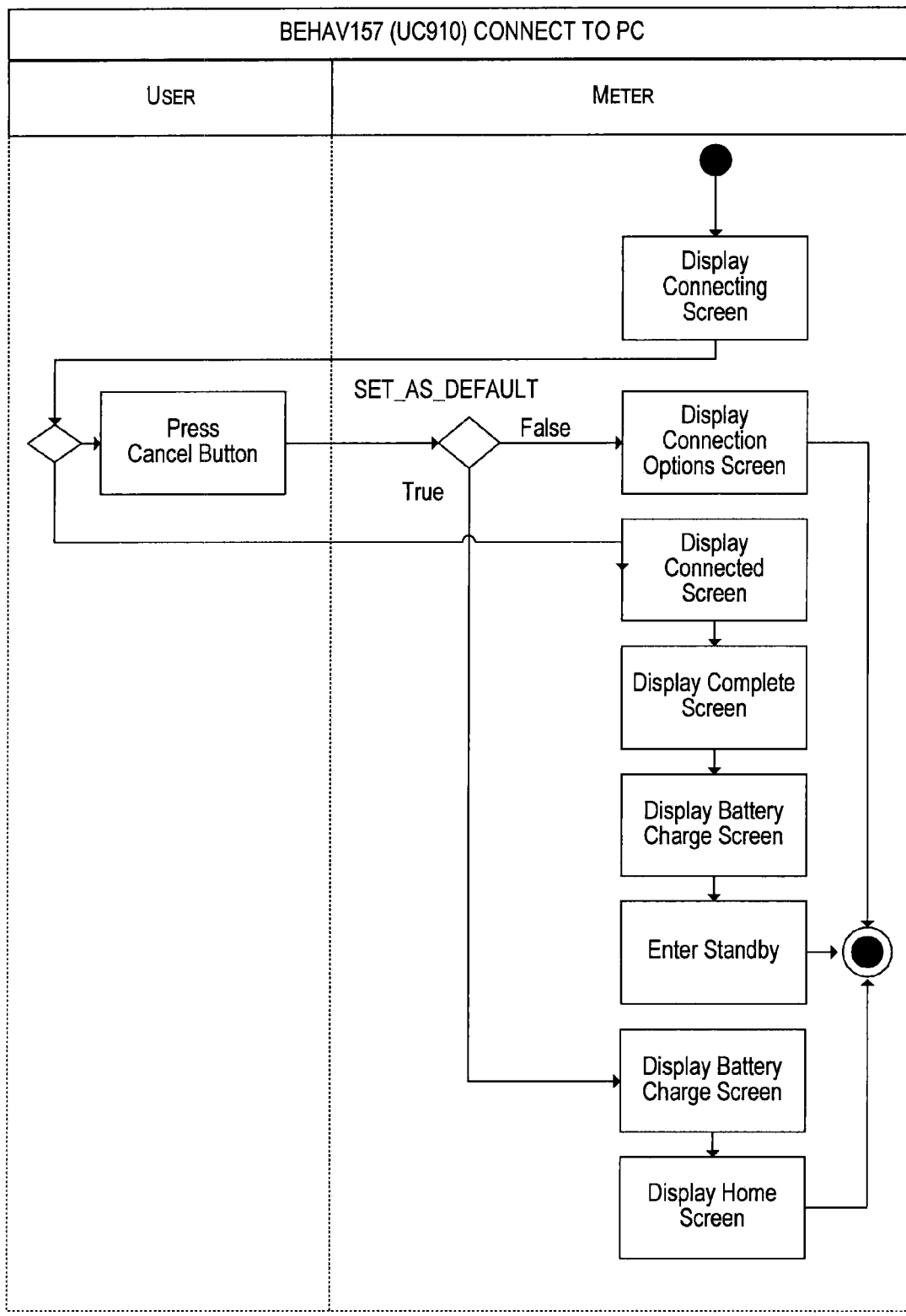
FIG. 7B is an activity diagram illustrating behavioral flow for connecting a diabetes manager to a PC according to the present teachings.

FIG. 7B is an activity diagram illustrating the behavioral flow for connecting the diabetes manager 104 to a computing device such as PC 106. With default settings, if the user presses the cancel button 704 while the connecting screen 700 is being displayed, the diabetes manager 104 shall cancel the attempts to connect with the PC 106, display a battery-charge screen for a specified time period, display the home screen 500, and/or enter a standby mode.

Without default settings, if the user presses the cancel button 704 while the connecting screen 700 is being displayed, the diabetes manager 104 shall cancel the attempts to connect with the PC 106 and display the connection-settings screen 1300. Alternatively, the diabetes manager 104 may display the home screen 500.

As stated earlier in reference to FIG. 2, the diabetes manager 104 may be connected to various types of devices (for example, the insulin pump 202 or 204, the CGM Device 200, the mobile device 302, the PC 106, or other healthcare devices 304). Before connecting to a device, it is important for the diabetes manager 104 to recognize what type of device is establishing a connection. For example, if the diabetes manager 104 is already connected to the insulin pump 202, it should not connect to the insulin pump 204 without first disconnecting from the insulin pump 202. This disconnection removes the risk of the patient 100 receiving the wrong dosage of insulin by having the diabetes manager 104 connected to more than one insulin-delivering device (such as insulin pump 202 or 204). As another example, the diabetes manager 104 is trying to establish a connection to a Continua manager (such as the PC 106, the mobile device 302, or the other health care device 304) and the diabetes manager 104 is connected to another device, such as insulin pump 202 or 204 or CGM Device 200, the diabetes manager 104 should disconnect from these devices before establishing a connection with the Continua manager (such as the PC 106, the mobile device 302, or the other health care device 304). Continua managers may operate to reconfigure or otherwise change settings or parameters on the diabetes manager which in turn affect its operation. Moreover, changes to the diabetes manager 104 could affect commands sent or interactions with the other devices, such as the insulin pump 202 or 204. Accordingly, it is advisable that the diabetes manager 104 disconnect from other devices before connecting to a Continua manager.

Figure 8:
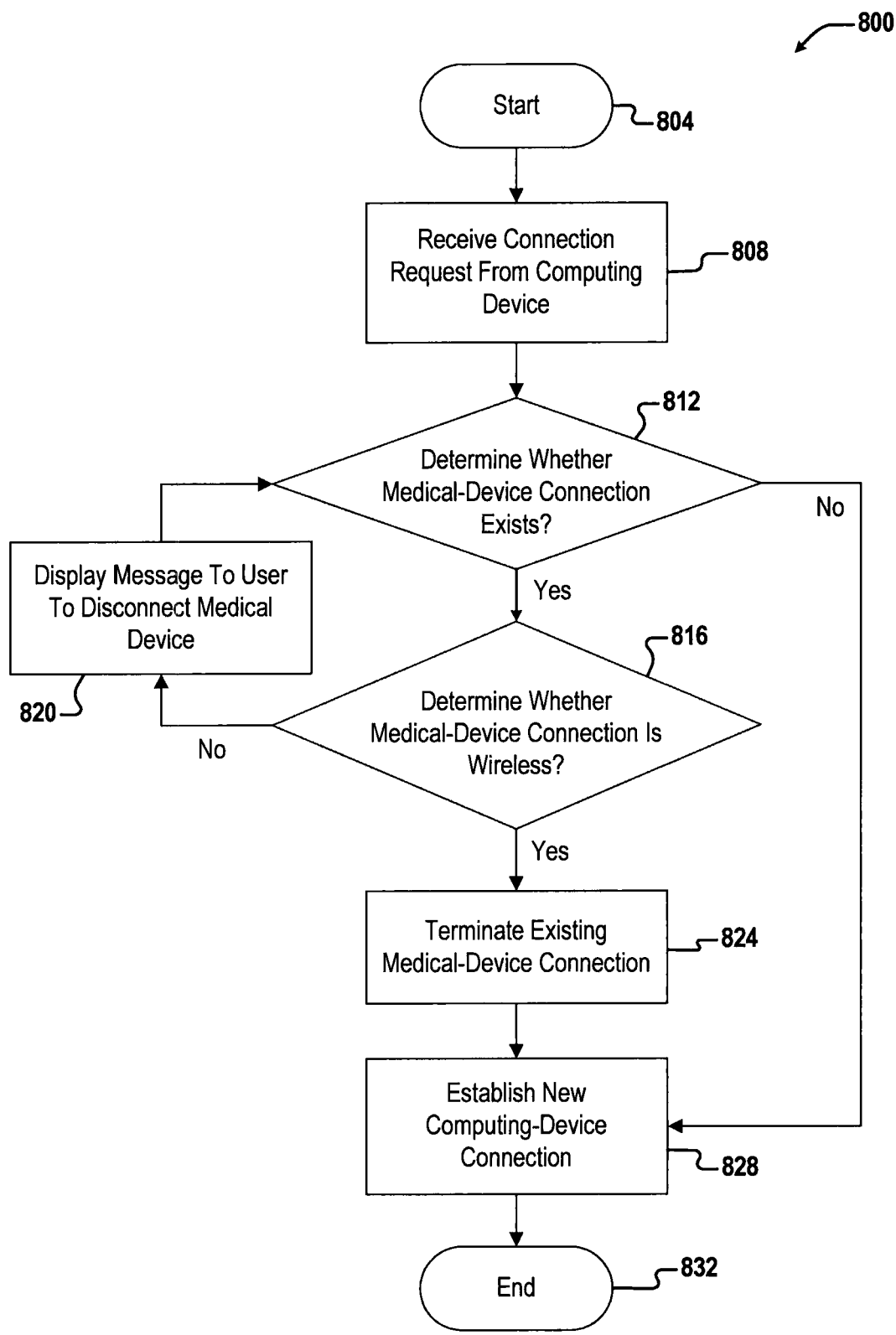
FIG. 8 illustrates a method of terminating an existing connection when establishing a new device connection according to the present teachings.

FIG. 8 depicts an exemplary method for establishing a data connection with a Continua manager, such as the PC 106. In the exemplary embodiment, a user initiates a data connection by pressing the connect-to-PC button 604 on the communication screen, thereby generating a request to establish a new data connection as indicated at 808. The request to establish a new data connection with the PC 106 is handled by the device-connectivity module 162.

First, a determination is made at 812 as to whether the diabetes manager 104 has any existing data connections, for example with the insulin pump 202 or 204 or another type of medical device. Because any existing data connection may be via wired or wireless connection, a determination is also made at 816 as to the type of data connection. If there are no existing data connections, the diabetes manager 104 will attempt to establish a new data connection at 828 as will be further described below.

Upon finding an existing wireless data connection, the diabetes manager 104 can terminate the existing data connection as indicated at 824. In some embodiments, a further determination may be made as to the type of device the existing data connection pertains to. The diabetes manager 104 may elect to terminate the existing data connection depending on the device type. For example, the diabetes manger may elect to terminate a data connection with an insulin pump but retain a data connection with a pulse oximeter or some other type of device. Conversely, upon finding a wired data connection, the diabetes manager 104 can prompt the user to disconnect the medical device, for example by displaying an appropriate message on a display of the diabetes manager 104, as shown at 820.

Once the existing data connection(s) have been terminated, the diabetes manager will attempt to establish a new data connection with the PC 106. To do so, diabetes manager 104 detects the presence of a wired connection with the PC 106. The diabetes manager 104 will establishes the new data connection using the wired connection, if present; otherwise, the diabetes manager 104 will establish the new data connection using a wireless data link, for example in accordance with the Bluetooth wireless technology standard. In either case, the diabetes manager establishes the new data connection at 828 by sending an association request to the PC 106 in accordance with IEEE standard 11073.

Referring again to FIG. 7B, if the cancel button is not pressed and the diabetes manager 104 connects successfully to the PC 106, the diabetes manager 104 shall display a connected screen. While the diabetes manager 104 is connected to the PC 106 and is transferring data, the diabetes manager 104 may display a data-transfer animation. While the diabetes manager 104 is connected to the PC 106 and is updating firmware, the diabetes manager 104 may display the text "Do not disconnect cable during update," and the diabetes manager 104 may display a firmware update animation. While the diabetes manager 104 is connected to the PC 106, the diabetes manager 104 shall disable an up volume button and a down volume button. While the diabetes manager 104 is connected to the PC 106 via a wired connection, the diabetes manager 104 shall prevent a BG test when the BG measurement strip 306 is inserted.

If the diabetes manager 104 detects a loss of communication to the PC 106, the diabetes manager 104 shall display a communication-lost message. Once the communication-lost message is acknowledged, for example, by pressing an okay button of the communication-lost message, the diabetes manager 104 shall enter the standby mode.

If a loss of USB connection is detected, the diabetes manager 104 shall display a connection-failed message. When the diabetes manager 104 is attempting to connect to the PC 106 via wireless connection, and the connection time has exceeded a specified time period, and the UI has not transitioned to the next screen, the diabetes manager 104 shall display the connection-failed message. Once the connection-failed message is acknowledged by pressing a yes button of the connection-failed message, the diabetes manager 104 shall attempt to reconnect to the PC 106. Once the connection-failed message is acknowledged by pressing a no button, the diabetes manager 104 shall display the home screen 500.

When the diabetes manager 104 has completed transferring data to and from the PC 106, the diabetes manager 104 shall display a data transfer complete screen. The diabetes manager 104 shall play a communication-complete sound if sound is enabled. The diabetes manager 104 shall not play the communication-complete sound if sound is not enabled. After the complete screen has been displayed for a specified time period, the diabetes manager 104 shall display the battery-charge screen for a specified time period and then enter the standby mode or return to the home screen.

Referring to FIG. 9, an exemplary set-up-new-pairing screen 900 of the diabetes manager 104 is illustrated. The set-up-new-pairing screen 900 may include various buttons (mechanical or touch buttons) that can be activated by touch or stylus or other selector device to display a corresponding detailed screen. The set-up-new-pairing screen 900 may include a devices button 904, a PCs button 908, and a back button 912. Pressing the back button 912 of the set-up-new-pairing screen 900 displays the communication screen 600.

Referring now to FIGS. 6A, 6B, and 9, pressing (or touching) the set-up-new-pairing button 608 of the communication screen 600 displays the set-up-new-pairing screen 900, if the number of devices the diabetes manager 104 is paired to is less than the maximum allowed number of devices. If the diabetes manager 104 is already paired with the maximum allowed number of devices, the diabetes manager 104 shall display a maximum-paired-devices message instead. Once the maximum-paired-devices message is acknowledged, for example, by pressing an okay button of the maximum-paired-devices message, the communication screen 600 is displayed.

Referring to FIGS. 6B, 9, 10B and 10C, pressing the devices button 904 of the set-up-new-pairing screen 900 displays a prepare-devices screen. The prepare-devices screen may include various buttons (mechanical or touch buttons) that can be activated by touch or stylus or other selector device to display a corresponding screen. The prepare-devices screen may include a cancel button and a next button. Pressing the cancel button of the prepare-devices screen displays the set-up-new-pairing screen 900.

Figure 10A:
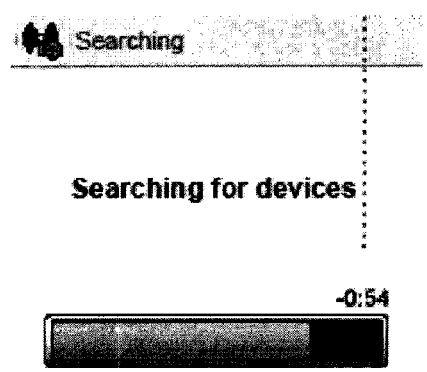
FIG. 10A is an exemplary searching-for-devices screen of a diabetes manager according to the present teachings.

Referring to FIG. 10A, an exemplary searching-for-devices screen 1000 of the diabetes manager 104 is illustrated. Referring now to FIGS. 10A, 10B and 10C, pressing the next button of the prepare-devices screen displays the searching-for-devices screen 1000. The searching-for-devices screen 1000 may include various buttons (mechanical or touch buttons) that can be activated by touch or stylus or other selector device to display a corresponding screen. The searching-for-devices screen 1000 may include a cancel button 1004. Pressing the cancel button 1004 of the searching-for-devices screen 1000 displays the set-up-new-pairing screen 900.

Figure 10D:
FIG. 10D is an exemplary devices-found screen of a diabetes manager according to the present teachings.
Figure 10D:
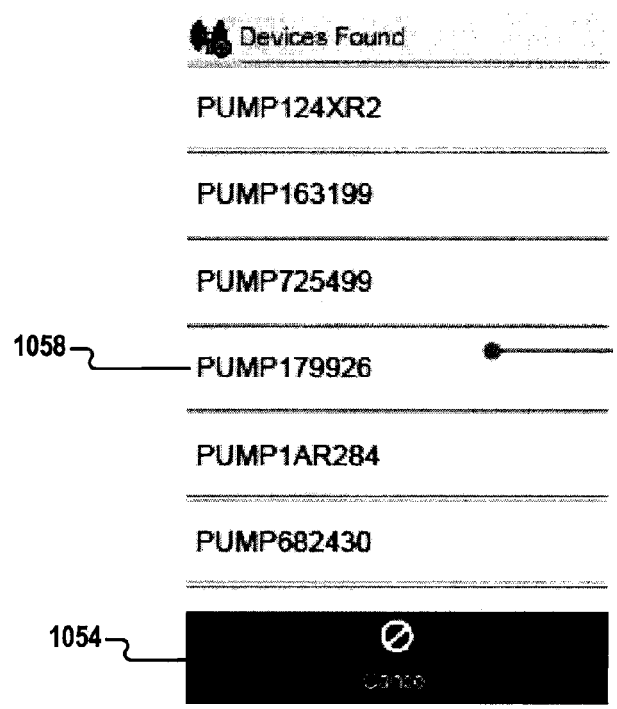
Figure 10B:
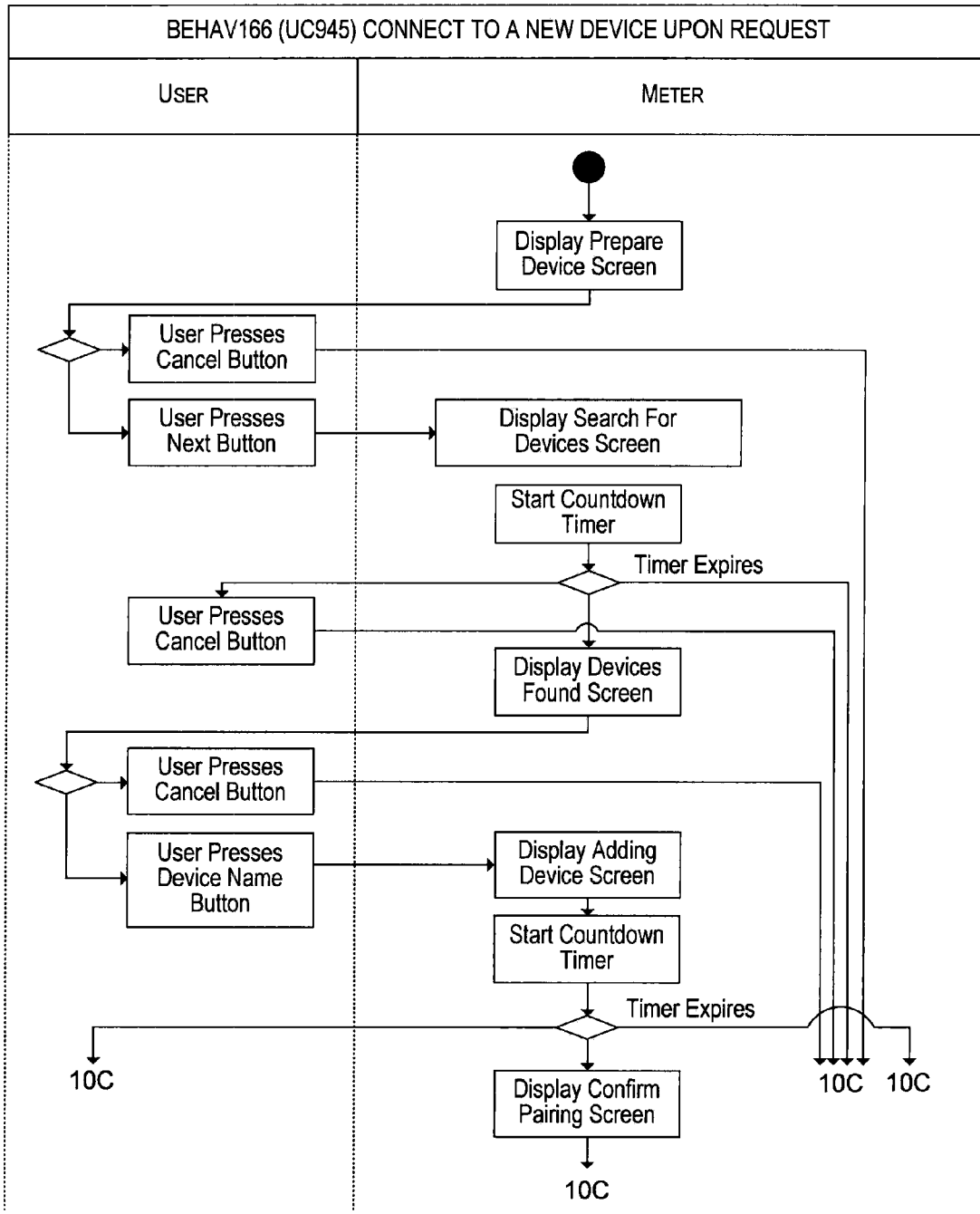
FIGS. 10B AND 10C are an activity diagram illustrating behavioral flow for setting up a new pairing between a diabetes manager and a device upon request according to the present teachings.
Figure 10C:
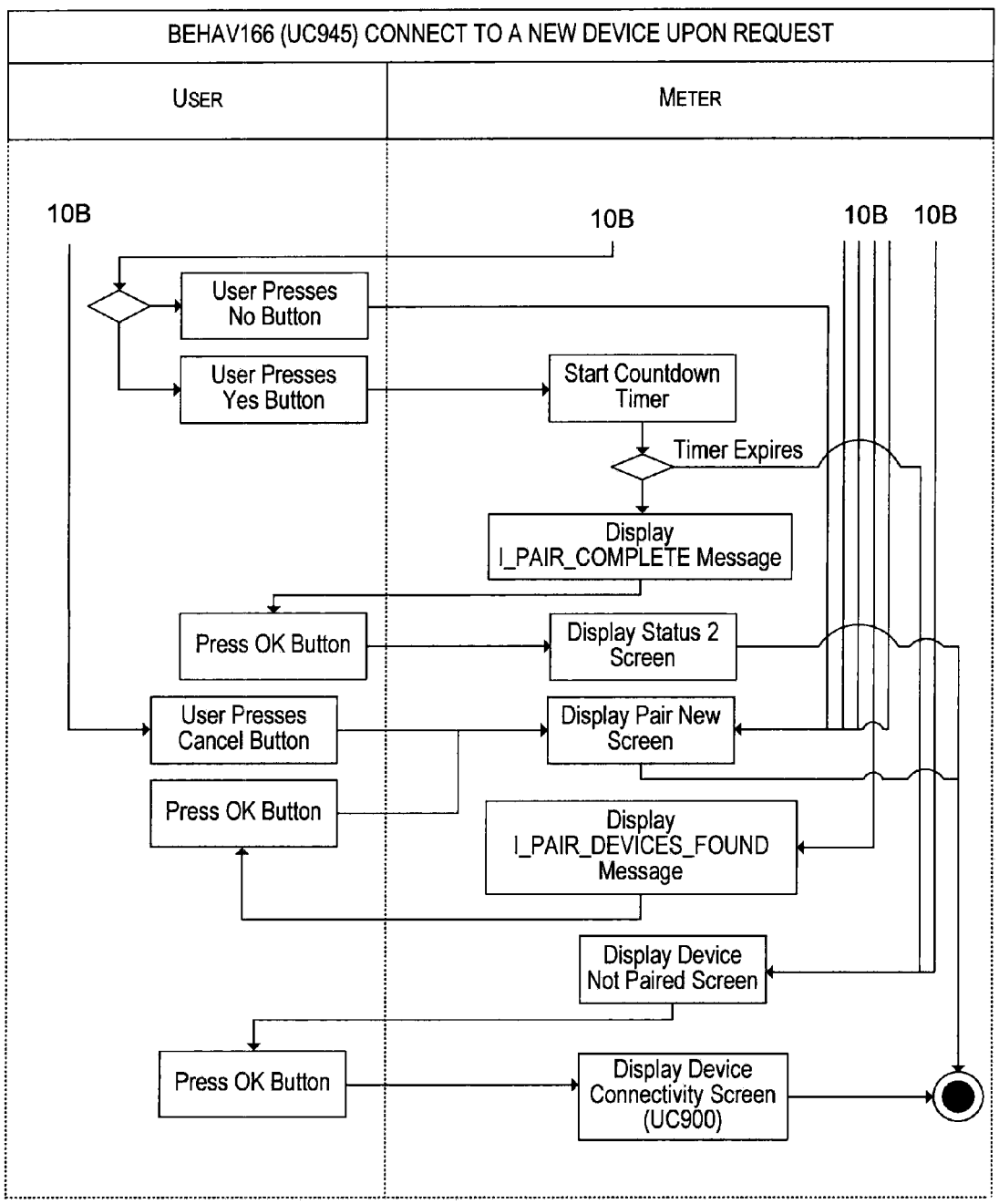

Referring now to FIGS. 10B 10C and 10D, while the diabetes manager 104 is searching for devices, the diabetes manager 104 shall associate each found device with a device-name button, such as the pump-179926 button 1058 of a devices-found screen 1050 (FIG. 10D). If a device is already paired to the diabetes manager 104, the diabetes manager 104 shall prevent this device from being associated with another device-name button. Once time exceeding a countdown timer associated with searching for devices has passed, and no devices are found, the diabetes manager 104 shall display a no-devices-found message. Once the no-devices-found message is acknowledged, for example, by pressing an okay button of the no-devices-found message, the diabetes manager 104 shall display the set-up-new-pairing screen 900. Once time exceeding the countdown timer associated with searching for devices has passed, and devices are found, the diabetes manager 104 shall display the devices-found screen 1050.

Referring still to FIG. 10D, the devices-found screen 1050 may include various buttons (mechanical or touch buttons) that can be activated by touch or stylus or other selector device to display a corresponding screen. The devices-found screen 1050 may include a cancel button 1054 and various device-name buttons, such as the pump-179926 button 1058. Pressing the cancel button 1054 displays the set-up-new-pairing screen 900.

If a pump (202 or 204) is already paired with the diabetes manager 104 and a device-name button associated with another pump is pressed, the diabetes manager 104 shall display an unpair-with-pump message. This is a safety precaution to prevent the diabetes manager 104 from actively controlling multiple pumps, which may be worn by different users. Once the unpair-with-pump message is acknowledged, for example, by pressing an okay button of the unpair-with-pump message, the diabetes manager 104 shall display the communication screen 600.

When a selected device-name button is pressed, for example, the pump-179926 button, the diabetes manager 104 shall display an adding-device screen. The adding-devices screen may include various buttons (mechanical or touch buttons) that can be activated by touch or stylus or other selector device to display a corresponding screen. The adding-devices screen may include a cancel button. Pressing the cancel button of the adding-device screen displays the set-up-new-pairing screen 900.

When the diabetes manager 104 successfully completes pairing with the selected device, for example, a pump 179926, the diabetes manager 104 shall display a confirm-pairing screen. The confirm-pairing screen may include various buttons (mechanical or touch buttons) that can be activated by touch or stylus or other selector device to display a corresponding screen. The confirm-pairing screen may include a yes button and a no button. When the no button of the confirm-pairing screen is pressed, the diabetes manager 104 shall discard the paired device information and display the set-up-new-pairing screen 900. When the yes button of the confirm-pairing screen is pressed, and the connect time exceeds a specified duration, the diabetes manager 104 shall display a device-not-paired screen. When the yes button of the confirm-pairing screen is pressed and the connect time does not exceed a specified duration, the diabetes manager 104 shall save the paired device information, set a home-screen-configuration value to STATUS, and display a pair-complete screen. The home-screen-configuration value determines which main screen is normally displayed: a status screen or a menu-type home screen.

The pair-complete screen may include various buttons (mechanical or touch buttons) that can be activated by touch or stylus or other selector device to display a corresponding screen. The pair-complete screen may include an okay button. When the okay button of the pair-complete screen is pressed, the diabetes manager 104 shall display the status screen (alternate home screen).

When the selected device is a pump (202 or 204), the diabetes manager 104 may display the text "Also press Confirm button on the pump."

If the diabetes manager 104 is not able to pair to the selected device, the diabetes manager 104 shall display the device-not-paired screen and may display the text "The meter was not able to pair with: <device identifier name>." If the diabetes manager 104 determines that the selected device is an insulin pump and it is already paired to another diabetes manager or other device with insulin pump control, the diabetes manager 104 may display the device-not-paired screen with the text: "The device <device identifier name> is already paired to a meter. Unpair the pump from the meter first." The device identifier name is a Bluetooth-friendly name. Once time exceeding a duration associated with adding devices has passed, and the screen has not transitioned to the next screen, the diabetes manager 104 shall display the device-not-paired screen.

Figure 11A:
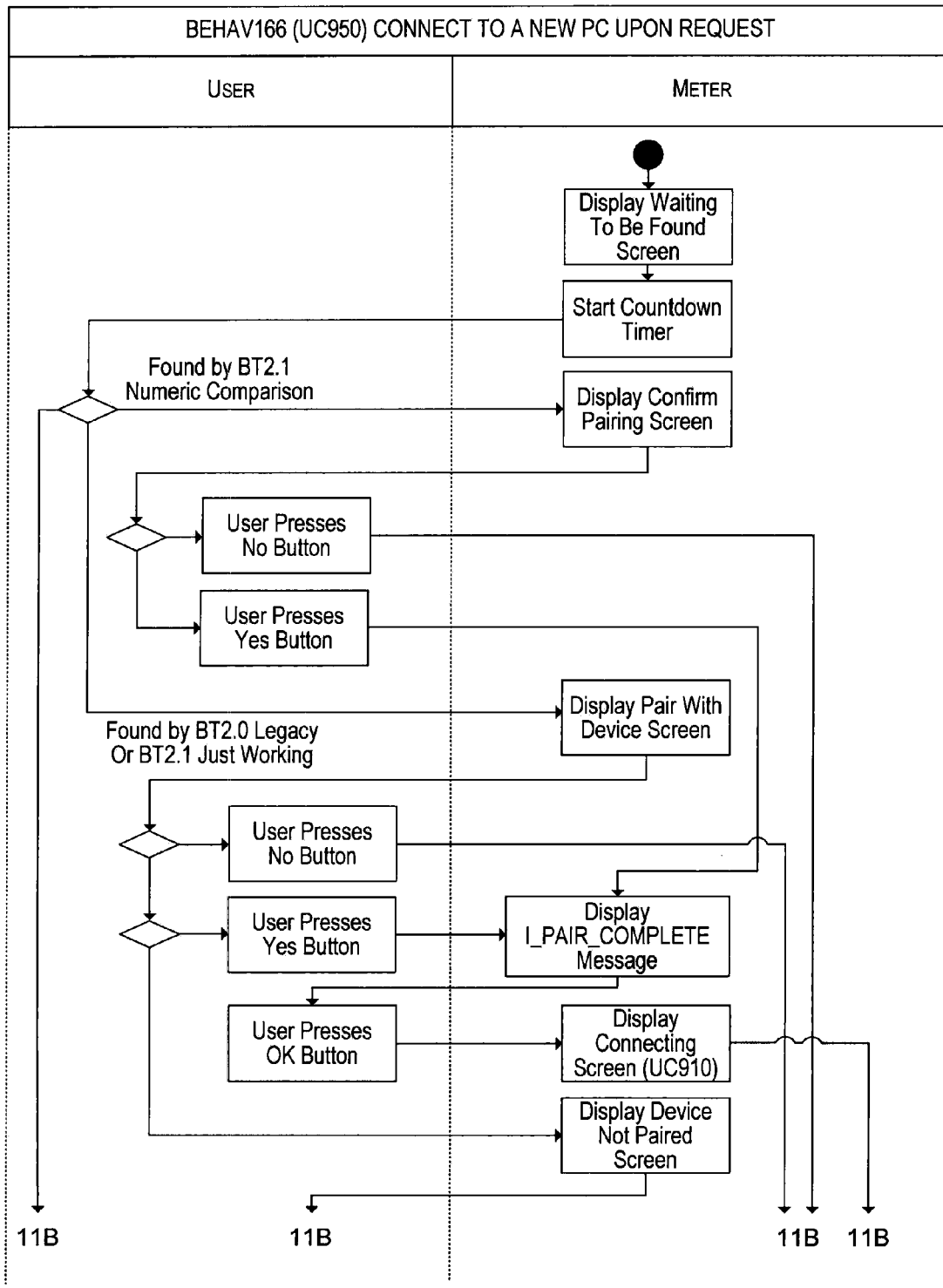
FIGS. 11A and 11B are an activity diagram illustrating behavioral flow for setting up a new pairing between a diabetes manager and a computing device upon request according to the present teachings.
Figure 11B:
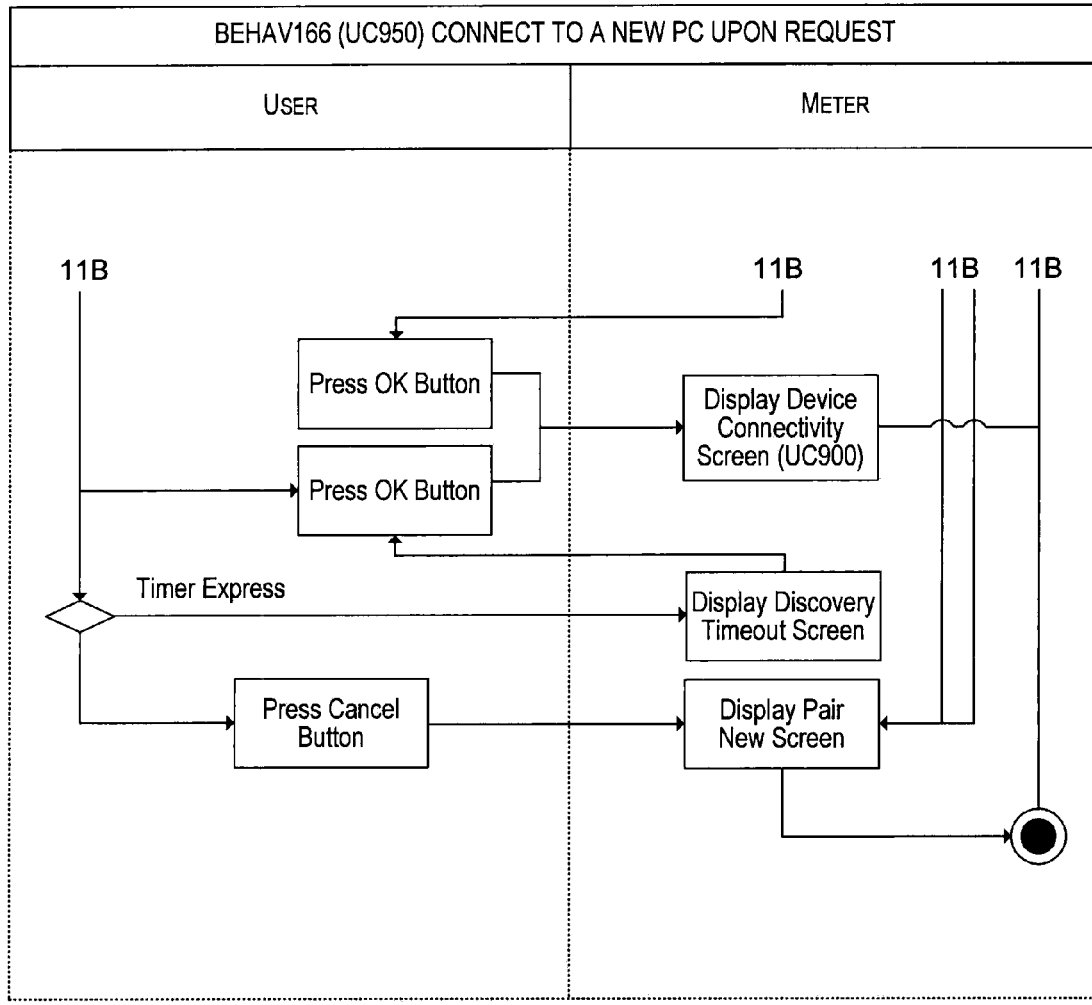

Referring to FIGS. 6B, 11A and 11B, pressing the PCs button 908 of the set-up-new-pairing screen 900 displays a waiting-to-be-found screen. When the waiting-to-be-found screen is displayed, the diabetes manager 104 shall set a discovery-mode countdown timer. The waiting-to-be-found screen may include various buttons (mechanical or touch buttons) that can be activated by touch or stylus or other selector device to display a corresponding screen. The waiting-to-be-found screen may include a cancel button. Pressing the cancel button of the waiting-to-be-found screen cancels the discovery-mode countdown timer and displays the set-up-new-pairing screen 900.

While the diabetes manager 104 is waiting to be found, the diabetes manager 104 shall display an amount of time remaining in a discovery mode. When the discovery-mode countdown timer expires, the diabetes manager 104 shall display a discovery-timeout screen. The discovery-timeout screen may include various buttons (mechanical or touch buttons) that can be activated by touch or stylus or other selector device to display a corresponding screen. The discovery-timeout screen may include an okay button. Pressing the okay button of the discovery-timeout screen cancels the discovery-mode countdown timer and displays the communication screen 600. If the diabetes manager 104 is unable to pair with the selected device, the diabetes manager 104 shall display the device-not-paired screen.

When the diabetes manager 104 is found by a device using Bluetooth version 2.1 or newer numeric comparison, the diabetes manager 104 shall display the confirm-pairing screen. The confirm-pairing screen may include various buttons (mechanical or touch buttons) that can be activated by touch or stylus or other selector device to display a corresponding screen. The confirm-pairing screen may include a no button and a yes button. Pressing the no button of the confirm-pairing screen discards device-pairing information for the selected device and displays the set-up-new-pairing screen 900. Pressing the yes button of the confirm-pairing screen displays the pair-complete screen once the diabetes manager 104 receives a confirmation from the selected device and saves paired device information for the selected device. Pressing the okay button of the pair-complete screen displays the connecting screen 700.

When the diabetes manager 104 is found by a device using Bluetooth version 2.1 or Bluetooth version 2.0 or older legacy, the diabetes manager 104 shall display a pair-with-device screen. The pair-with-device screen may include various buttons (mechanical or touch buttons) that can be activated by touch or stylus or other selector device to display a corresponding screen. The pair-with-device screen may include a no button and a yes button. Upon pressing the no button of the pair-with-device screen, the diabetes manager 104 shall display the set-up-new-pairing screen 900. Upon pressing the yes button of the pair-with-device screen, the diabetes manager 104 shall pair with the device and display the pair-complete screen. Pressing the okay button of the pair-complete screen displays the connecting screen 700.

Figure 12A:
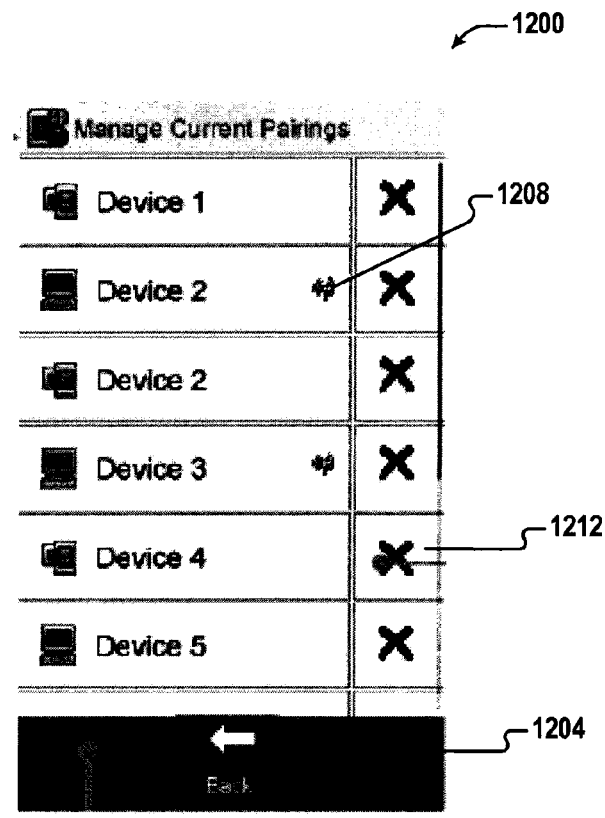
FIG. 12A is an exemplary manage-current-pairings screen of a diabetes manager according to the present teachings.

Referring to FIG. 12A, an exemplary manage-current-pairings screen 1200 of the diabetes manager 104 is illustrated. The diabetes manager 104 shall display all devices at the top of the list followed by PCs and managers on the manage-current-pairings screen 1200. If a paired device/PC is currently not connected, the meter shall hide a radio connection icon 1208 corresponding to that paired device/PC.

Figure 12B:
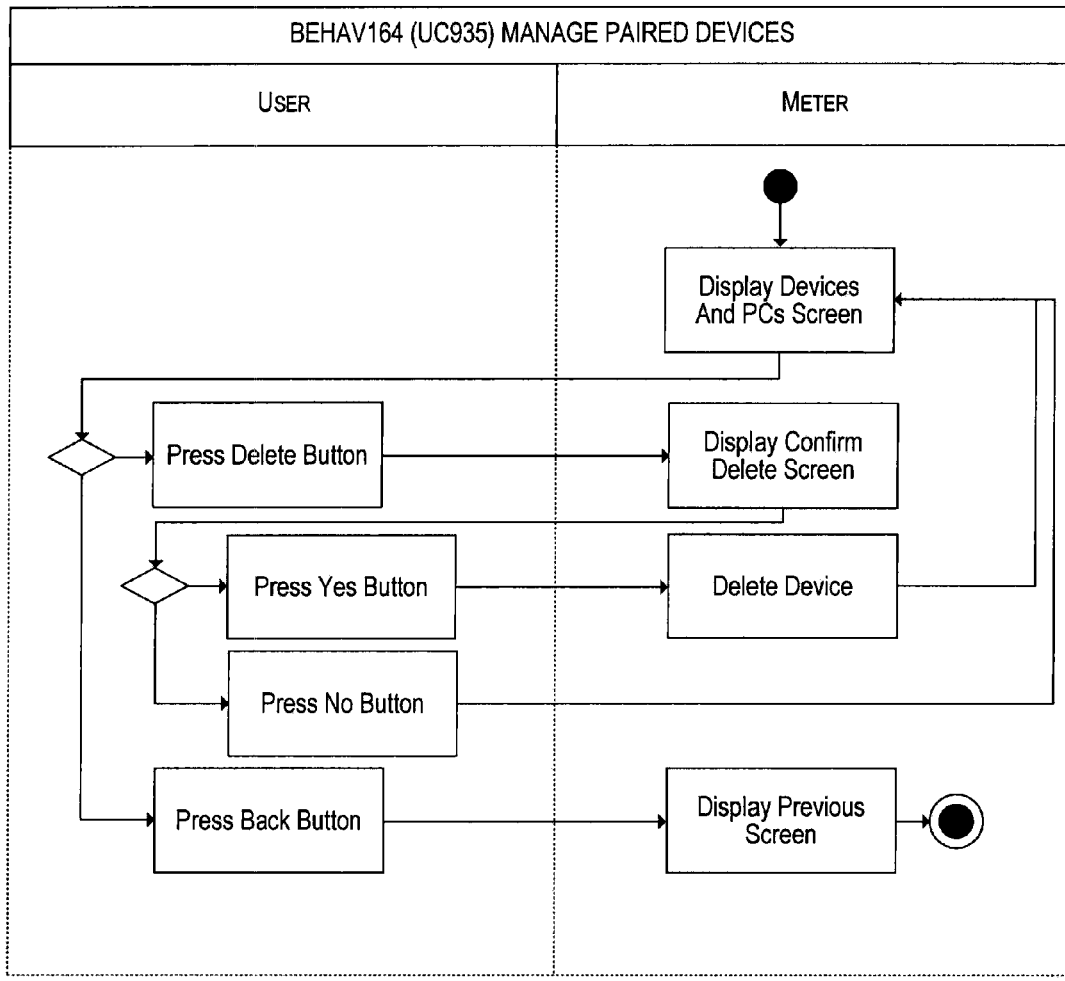
FIG. 12B is an activity diagram illustrating behavioral flow for managing devices paired with a diabetes manager according to the present teachings.

Referring now to FIGS. 6B, 12A, and 12B, pressing (or touching) the manage-current-pairings button 612 of the communication screen 600 displays the manage-current-pairings screen 1200. The manage-current-pairings screen 1200 may include various buttons (mechanical or touch buttons) that can be activated by touch or stylus or other selector device to display a corresponding screen. The manage-current-pairings screen 1200 may include a back button 1204 and various delete buttons that correspond to various paired devices, for example, device-4 delete button 1212.

Pressing the back button 1204 of the manage-current-pairings screen 1200 displays the communication screen 600. When no devices are paired, the diabetes manager 104 may display the text "No devices are paired."

Referring to FIGS. 12A and 12B, when the user presses one of the delete buttons that correspond to the various paired devices, for example, device-4 delete button 1212, the diabetes manager 104 shall display a confirm-delete screen. The confirm-delete screen may include various buttons (mechanical or touch buttons) that can be activated by touch or stylus or other selector device to display a corresponding screen. The confirm-delete screen may include a no button and a yes button.

Pressing the no button of the confirm-delete screen displays the manage-current-pairings screen 1200 without deleting the selected paired device, for example, device 4.

Pressing the yes button of the confirm-delete screen deletes the selected paired device, updates a list of paired devices, and displays the manage-current-pairings screen 1200. If the selected paired device is a pump, the diabetes manager 104 shall set the home-screen-configuration value to "Main Menu" and set a bolus-threshold value to maximum.

Figure 13A:
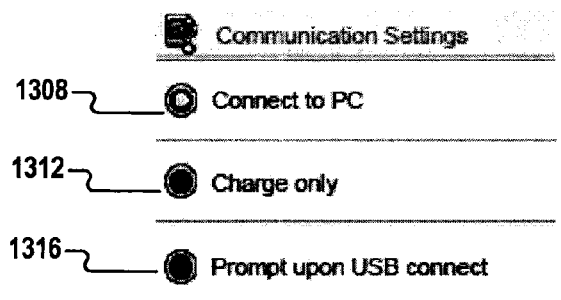
FIG. 13A is an exemplary connection-settings screen of a diabetes manager according to the present teachings.
Figure 13A:
Figure 13B:
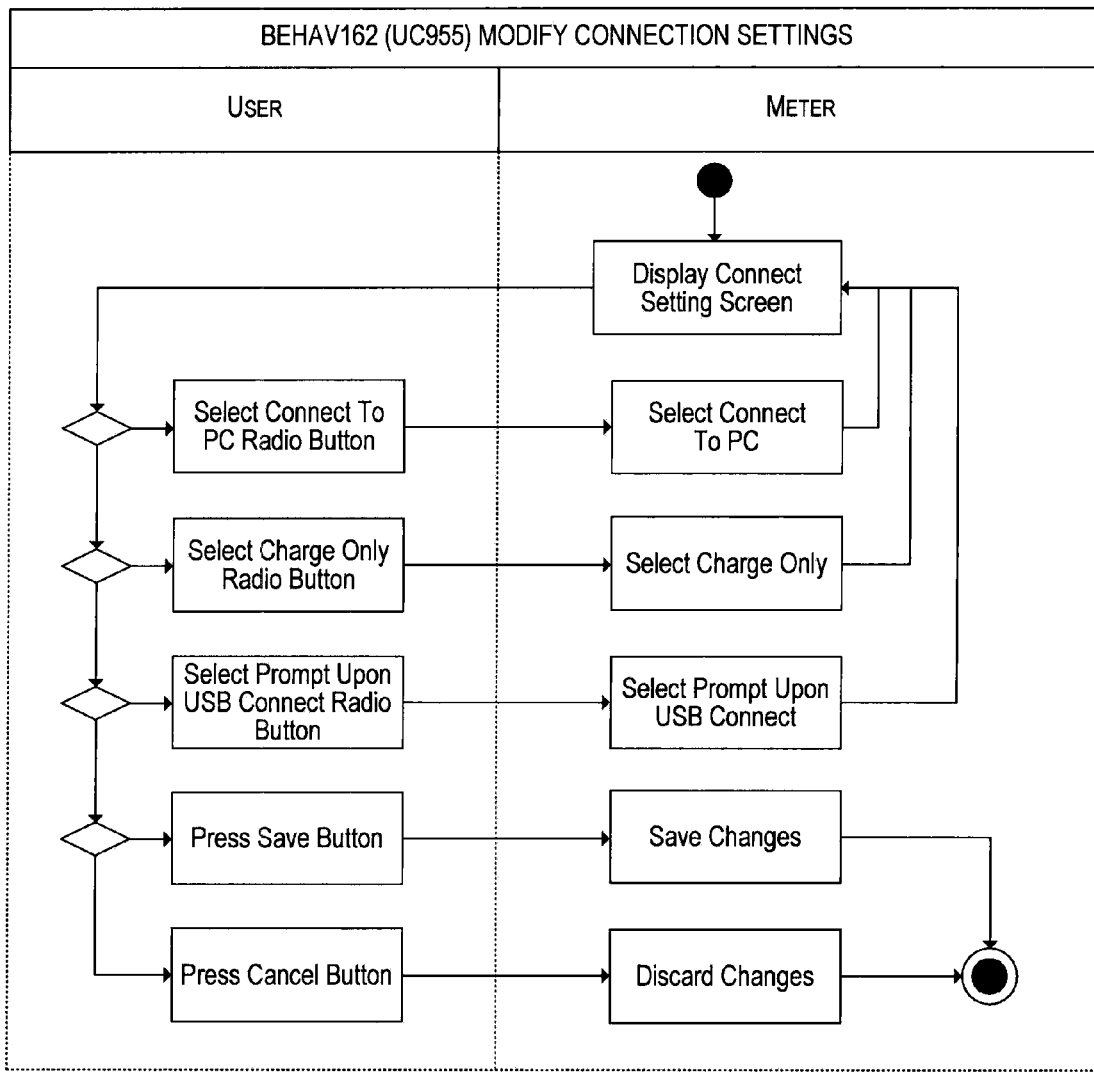
FIG. 13B is an activity diagram illustrating behavioral flow for modifying connection settings for a diabetes manager according to the present teachings.

Referring now to FIG. 13A, an exemplary connection-settings screen 1300 of the diabetes manager 104 is illustrated. Referring now to FIGS. 6B, 13A, and 13B, pressing (or touching) the settings button 616 of the communication screen 600 displays the connection-settings screen 1300. The connection-settings screen 1300 may include various buttons (mechanical or touch buttons) that may be activated by touch or stylus or other selector device to display a corresponding screen. The connection-settings screen 1300 may include a cancel button 1304, a connect-to-PC radio button 1308, a charge-only radio button 1312, a prompt-upon-USB-connect radio button 1316, and a save button 1320.

Pressing the cancel button 1304 of the connection-settings screen 1300 returns the user to a point of entry (whatever screen the user was on before the connection-settings screen 1300) and discards any changes.

Pressing the connect-to-PC radio button 1304 of the connection-settings screen 1300 selects the connect-to-PC radio button 1304 and sets a CONNECT_TO_PC_VAL to true, a CHARGE_ONLY_VAL to false, a PROMPT_UPON_USB_VAL to false, and a SET_AS_DEFAULT_VAL to true.

Pressing the charge-only radio button 1308 of the connection-settings screen 1300 selects the charge-only radio button 1308 and sets the CHARGE_ONLY_VAL to true, the CONNECT_TO_PC_VAL to false, the PROMPT_UPON_USB_VAL to false, and the SET_AS_DEFAULT_VAL to true.

Pressing the prompt-upon-USB-connect radio button 1316 of the connection-settings screen 1300 selects the prompt-upon-USB-connect radio button 1316; sets the PROMPT_UPON_USB_VAL to true, the SET_AS_DEFAULT_VAL to false, the CONNECT_TO_PC_VAL to false, and the CHARGE_ONLY_VAL to false; and displays the connection-settings screen 1300 upon subsequent establishment of a USB connection.

Pressing the save button 1320 of the connection-settings screen 1300 while the connect-to-PC radio button 1304 is selected sets a USB enumeration type to indicate a PC data connection and returns to the point of entry. Pressing the save button 1320 while the charge-only radio button 1308 is selected sets the USB enumeration type to indicate charging mode and returns to the point of entry.

Figure 14A:
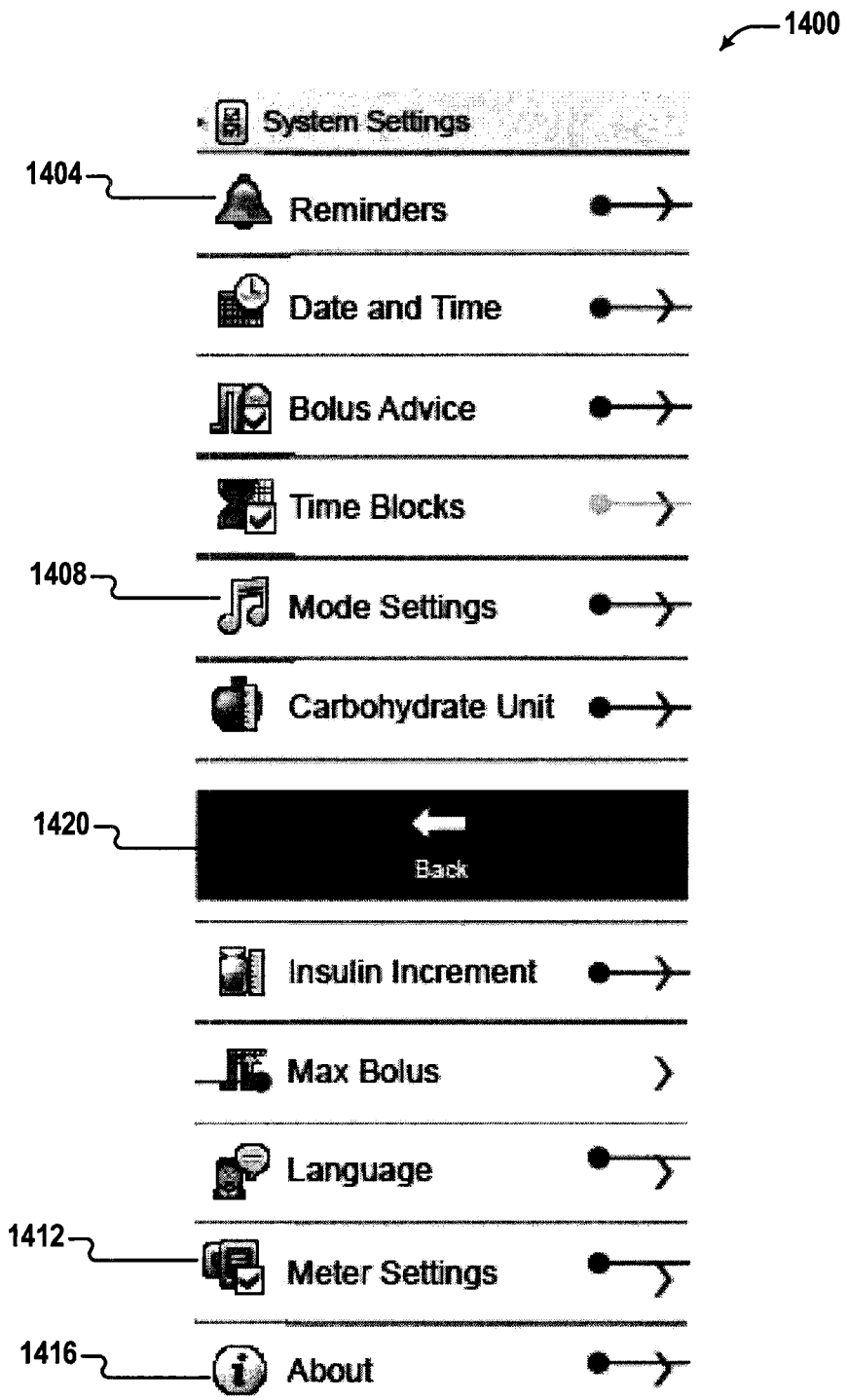
FIG. 14A is an exemplary system-settings screen of a diabetes manager according to the present teachings.

Referring now to FIG. 14A, an exemplary system-settings screen 1400 of the diabetes manager 104 is illustrated. Pressing (or touching) the settings button 516 of the home screen 500 displays the system-settings screen 1400. The system-settings screen 1400 may include various buttons (mechanical or touch buttons) that can be activated by touch or stylus or other selector device to display a corresponding detailed screen. The system-settings screen 1400 may include a reminders button 1404, a mode-settings button 1408, a meter-settings button 1412, an about button 1416, and a back button 1420. Some of the buttons may not be visible on the screen as displayed. By scrolling up on the system-settings screen 1400, using touch or a stylus, for example, will bring the lower, additional menu buttons shown under the back button 1420 in FIG. 14A into view. Pressing the back button 1420 displays the home screen 500.

Figure 14B:
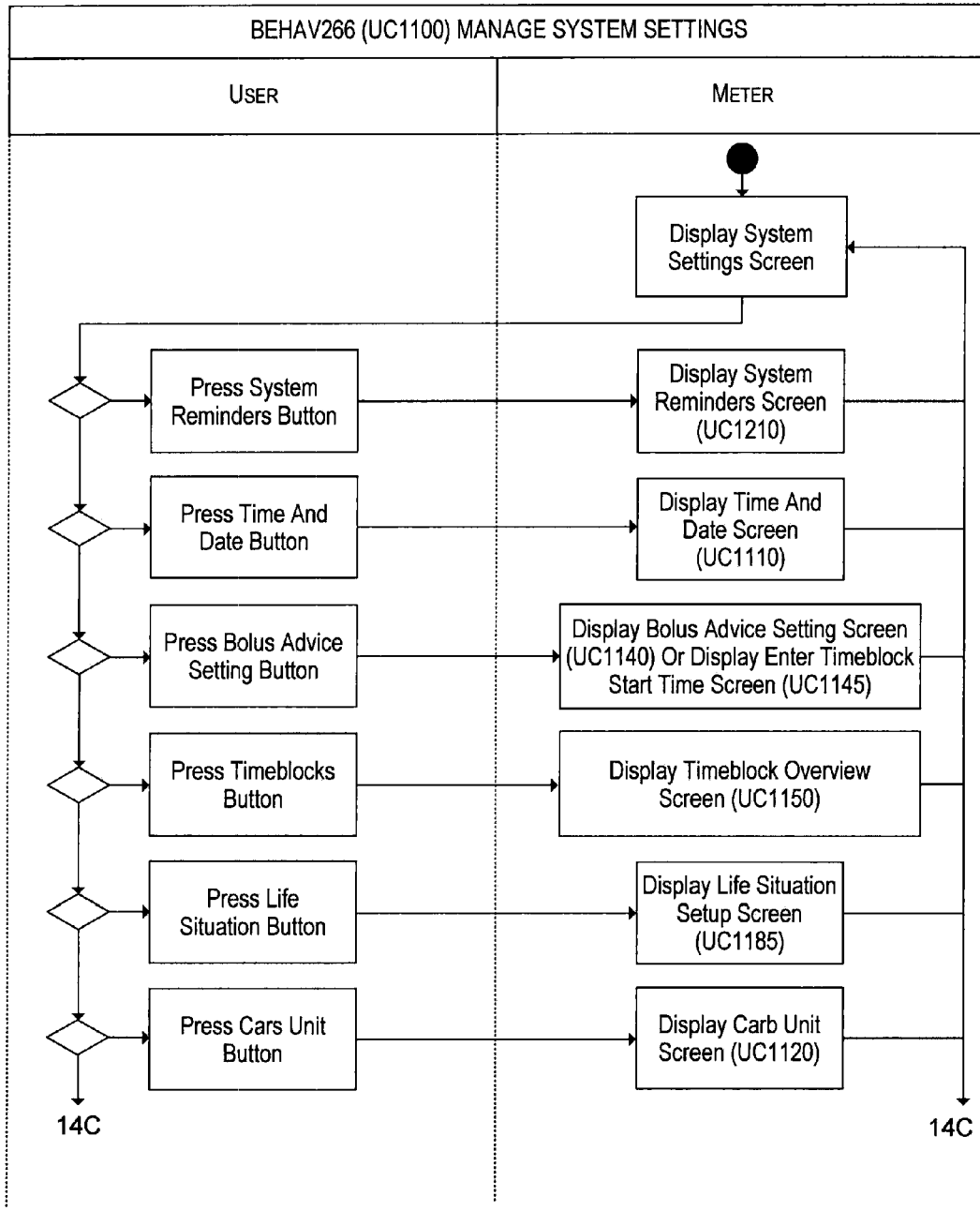
FIGS. 14B and 14C are an activity diagram illustrating behavioral flow for managing system settings for a diabetes manager according to the present teachings.
Figure 14C:
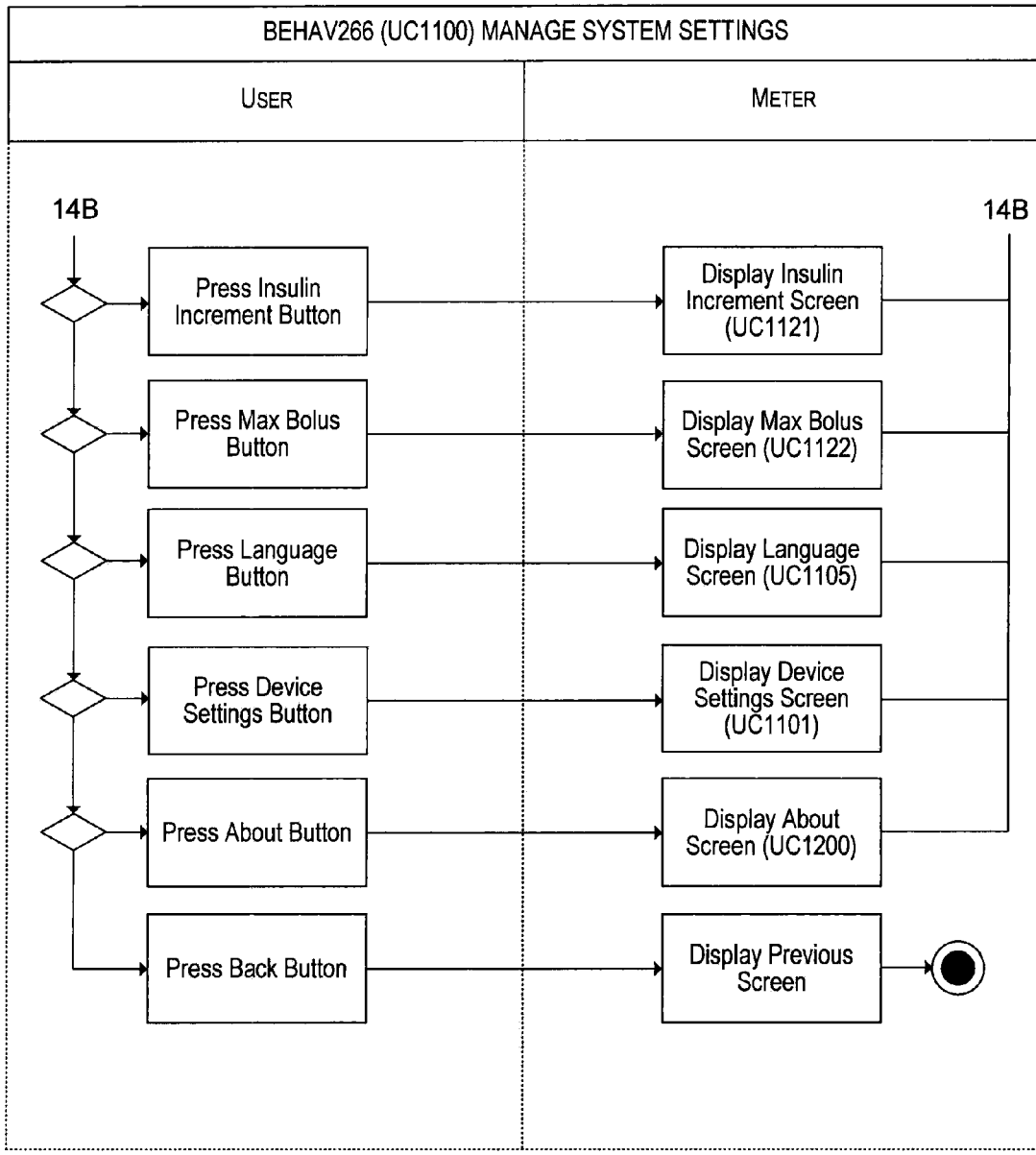

FIGs. 14B and 14C serve as a use case map of the system-settings module 160, illustrating the behavioral flow for modifying the settings of the diabetes manager 104. The behavioral flows for setting and managing reminders, viewing and changing time and date, viewing and changing bolus advice settings, viewing and changing timeblocks, viewing and changing mode settings, viewing and changing carbohydrates, viewing and changing insulin increment (only if NOT connected to a pump), viewing and changing max bolus (only if NOT connected to a pump), viewing and changing the language, viewing and changing meter settings, and viewing information about the diabetes manager 104 are illustrated.

Figure 15A:
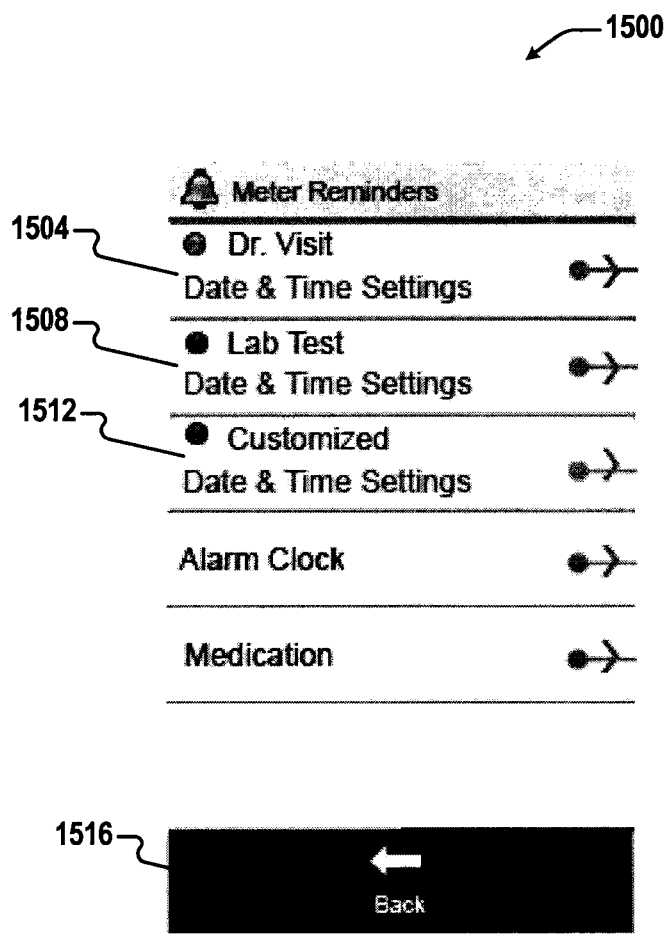
FIG. 15A is an exemplary reminders screen of a diabetes manager according to the present teachings.

FIG. 15A illustrates an exemplary reminders screen 1500 of the diabetes manager 104. With reference to FIGS. 14A, 14B, 14C and 15A, pressing (or touching) the reminders button 1404 of the system-settings screen 1400 displays the reminders screen 1500. The reminders screen 1500 may include various buttons (mechanical or touch buttons) that can be activated by touch or stylus or other selector device to display a corresponding screen. The reminders screen 1500 may include a doctor-visit button 1504, a lab-test button 1508, a custom button 1512, and a back button 1516. Pressing the back button 1516 displays the system-settings screen 1400.

Figure 16:
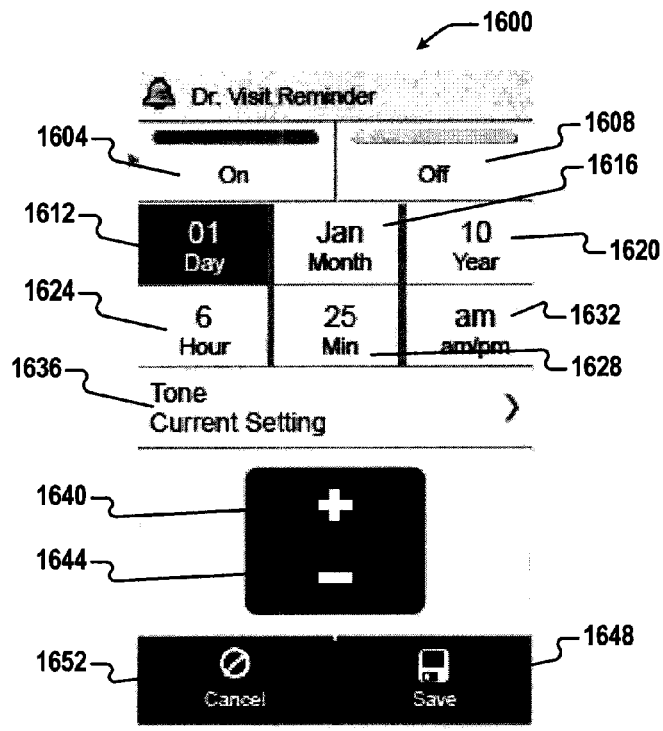
FIG. 16 is an exemplary doctor-visit screen of a diabetes manager according to the present teachings.

FIG. 16 illustrates an exemplary doctor-visit screen 1600 of the diabetes manager 104. When there are no doctor-visit reminders to display (the value of a DR_VISIT_REMINDER_ENABLED_VAL is false), the diabetes manager 104 shall display an inactive icon on the doctor-visit button 1504.

When there is at least one doctor-visit reminder to display (the value of a DR_VISIT_REMINDER_ENABLED_VAL is true), the diabetes manager 104 shall display an active icon on the doctor-visit button 1504.

Figure 15B:
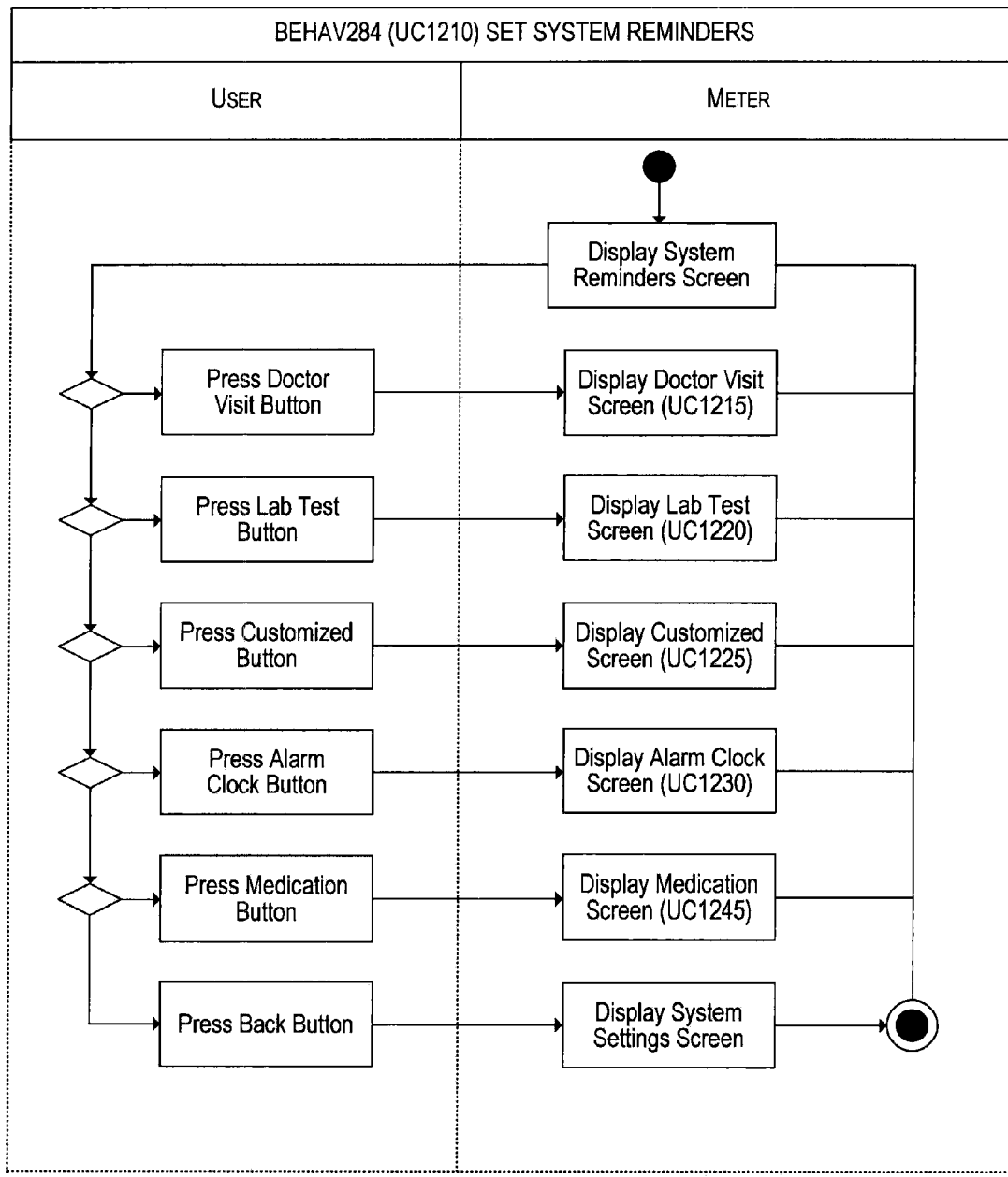
FIG. 15B is an activity diagram illustrating behavioral flow for setting system reminders for a diabetes manager according to the present teachings.

Referring to FIGS. 15A, 15B, and 16, pressing (or touching) the doctor-visit button 1504 of the reminders screen 1500 displays the doctor-visit screen 1600. The doctor-visit screen 1600 may include various buttons (mechanical or touch buttons) that can be activated by touch or stylus or other selector device to display a corresponding screen. The doctor-visit screen 1600 may include an on button 1604, an off button 1608, a day button 1612, a month button 1616, a year button 1620, an hour button 1624, a minute button 1628, an AM/PM button 1632, a tone button 1636, an up button 1640, a down button 1644, a save button 1648, and a cancel button 1652. Pressing the cancel button 1652 displays the reminders screen 1500.

Figure 17:
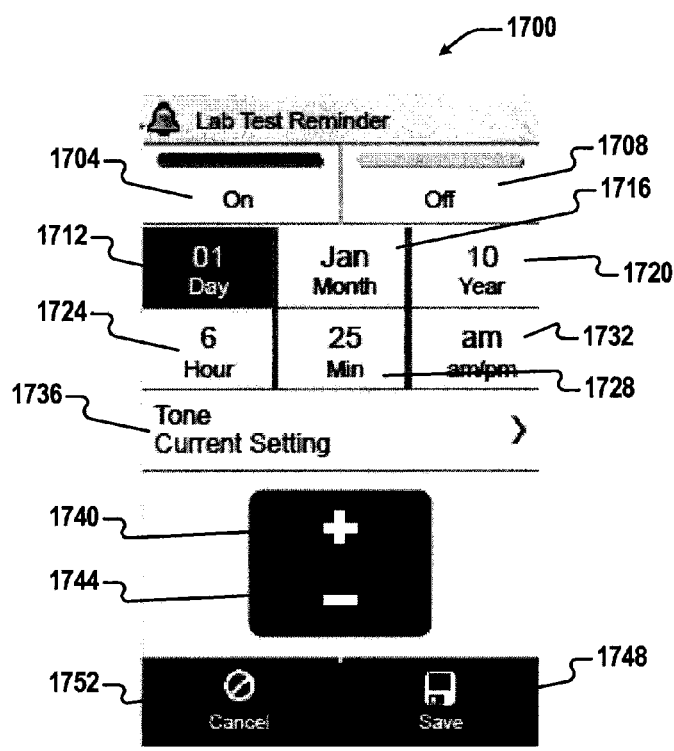
FIG. 17 is an exemplary lab-test screen of a diabetes manager according to the present teachings.

FIG. 17 illustrates an exemplary lab-test screen 1700 of the diabetes manager 104. When there are no lab-test reminders to display (the value of a LAB_TEST_REMINDER_ENABLED_VAL value is false), the diabetes manager 104 shall display an inactive icon on the lab-test button 1508. When there is at least one lab-test reminder to display (the value of the LAB_TEST_REMINDER_ENABLED_VAL value is true), the diabetes manager 104 shall display an active icon on the lab-test button 1508.

Referring to FIGS. 15A, 15B, and 17, pressing (or touching) the lab-test button 1508 of the reminders screen 1500 displays the lab-test screen 1700. The lab-test screen 1700 may include various buttons (mechanical or touch buttons) that can be activated by touch or stylus or other selector device to display a corresponding screen. The lab-test screen 1700 may include an on button 1704, an off button 1708, a day button 1712, a month button 1716, a year button 1720, an hour button 1724, a minute button 1728, an AM/PM button 1732, a tone button 1736, an up button 1740, a down button 1744, a save button 1748, and a cancel button 1752. Pressing the cancel button 1752 displays the reminders screen 1500.

FIG. 18 illustrates an exemplary custom screen 1800 of the diabetes manager 104. When there are no custom reminders to display (the value of a CUSTOM_REMINDER_ENABLED_VAL value is false), the diabetes manager 104 shall display an inactive icon on custom button 1512. When there is at least one custom reminder to display (the value of the CUSTOM_REMINDER_ENABLED_VAL value is true), the diabetes manager 104 shall display an active icon on the custom button 1512.

Referring to FIGS. 15A, 15B, and 18, pressing (or touching) the custom button 1512 of the reminders screen 1500 displays the custom screen 1800. The custom screen 1800 may include various buttons (mechanical or touch buttons) that can be activated by touch or stylus or other selector device to display a corresponding screen. The custom screen 1800 may include an on button 1804, an off button 1808, a day button 1812, a month button 1816, a year button 1820, an hour button 1824, a minute button 1828, an AM/PM button 1832, a tone button 1836, an up button 1840, a down button 1844, a save button 1848, and a cancel button 1852. Pressing the cancel button 1852 displays the reminders screen 1500.

FIG. 19A illustrates an exemplary mode-settings screen 1900 of the diabetes manager 104. With reference to FIGS. 14A, 14B, 14C and 19A, pressing (or touching) the mode-settings button 1408 of the system-settings screen 1400 displays the mode-settings screen 1900. The mode-settings screen 1900 may include various buttons (mechanical or touch buttons) that can be activated by touch or stylus or other selector device to display a corresponding screen. The mode-settings screen 1900 may include a normal button 1904, a vibrate button 1908, a quiet button 1912, a loud button 1916, a signal-suspension button 1920, a save button 1924, and a cancel button 1928.

Figure 19B:
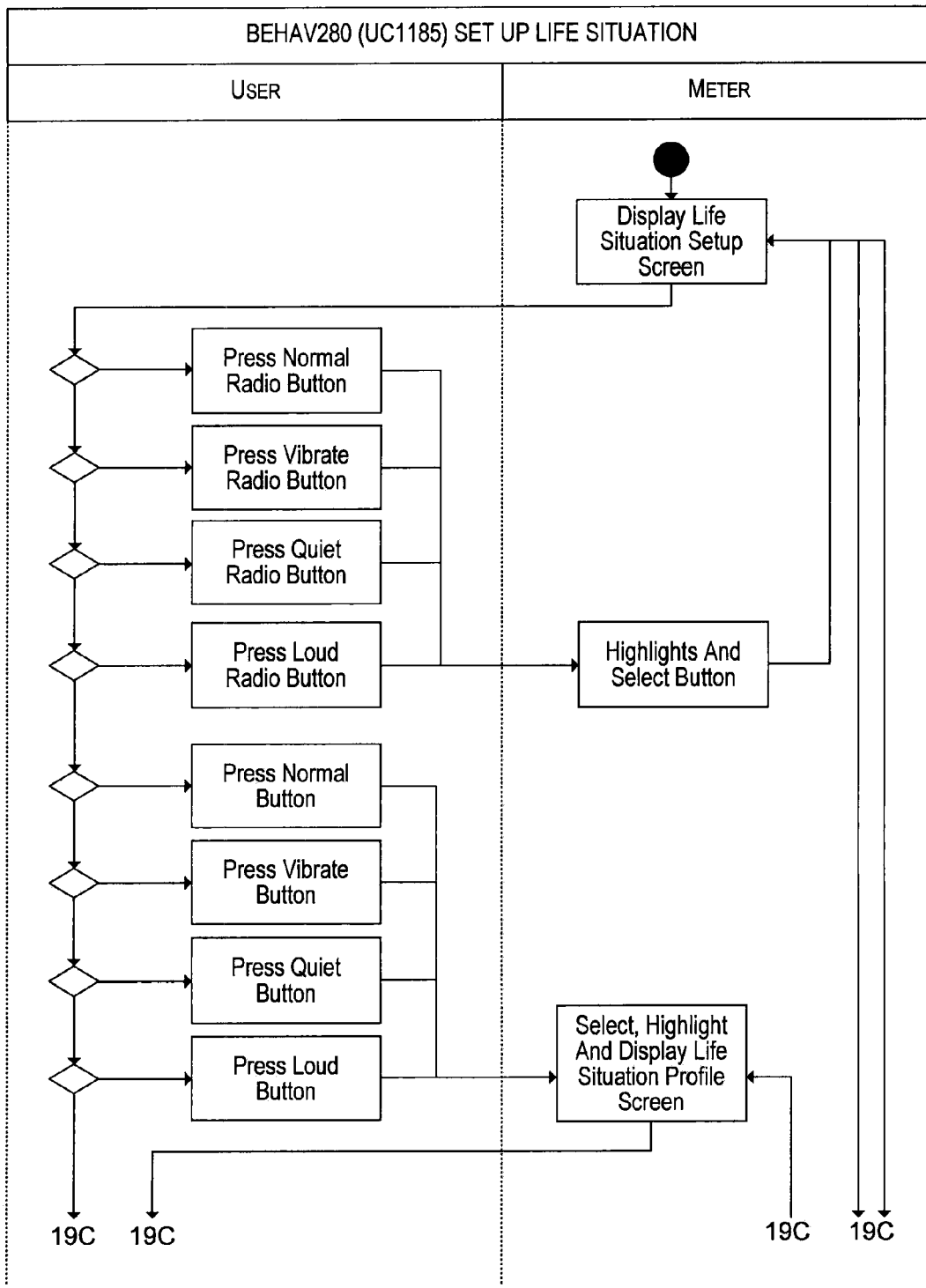
FIGS. 19B and 19C are an activity diagram illustrating behavioral flow for setting different modes for a diabetes manager according to the present teachings.
Figure 19C:
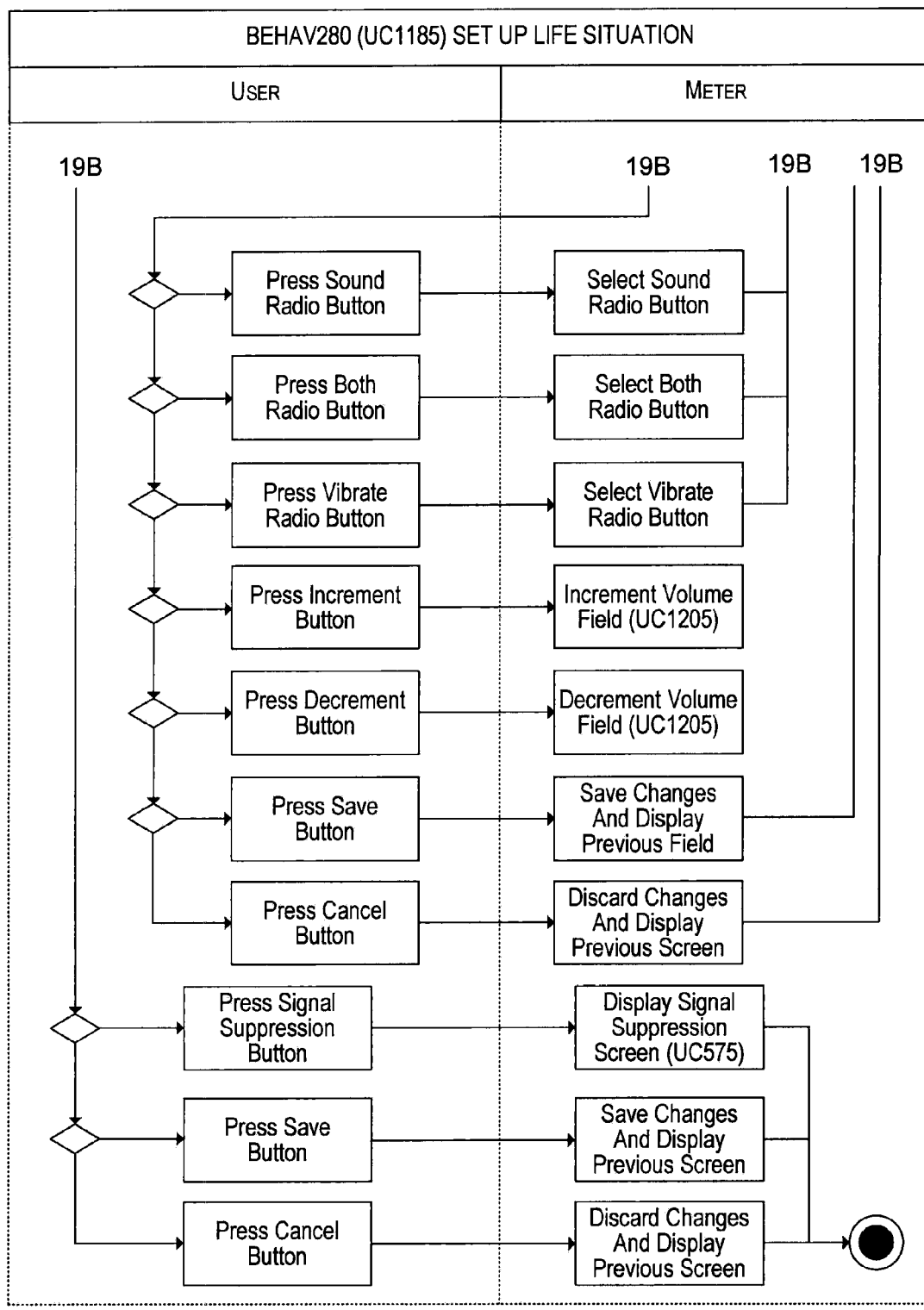

Referring to FIGS. 19A, 19B and 19C, pressing the save button 1924 saves the current settings and displays the system-settings screen 1400 (or other point of entry). Pressing the cancel button 1928 displays the system-settings screen 1400 (or other point of entry) without making any changes. Pressing the normal button 1904, the vibrate button 1908, the quiet button 1912, or the loud button 1916 highlights the selected radio button and displays a life-situation -profile screen.

Still referring to FIGS. 19A, 19B and 19C, when the value of a METER_SIGNAL_SUPPRESSION_ENABLE_VAL is true, the diabetes manager 104 shall display an active icon on signal-suspension button 1920. When the value of a METER_SIGNAL_SUPPRESSION_ENABLE_VAL is false, the diabetes manager 104 shall display an inactive icon on signal-suspension button 1920. Pressing the signal-suspension button 1920 displays a signal-suspension screen.

FIG. 20A illustrates an exemplary meter-settings screen 2000 of the diabetes manager 104. With reference to FIGS. 14A, 14B, 14C and 20A, pressing (or touching) the meter-settings button 1412 of the system-settings screen 1400 displays the meter-settings screen 2000. The meter-settings screen 2000 may include various buttons (mechanical or touch buttons) that can be activated by touch or stylus or other selector device to display a corresponding screen. The meter-settings screen 2000 may include a brightness button 2004, a home-screen button 2008, a touchscreen button 2012, a background-color button 2016, a meter-function-test button 2020, a screen-calibration button 2024, and a back button 2028.

Figure 20B:
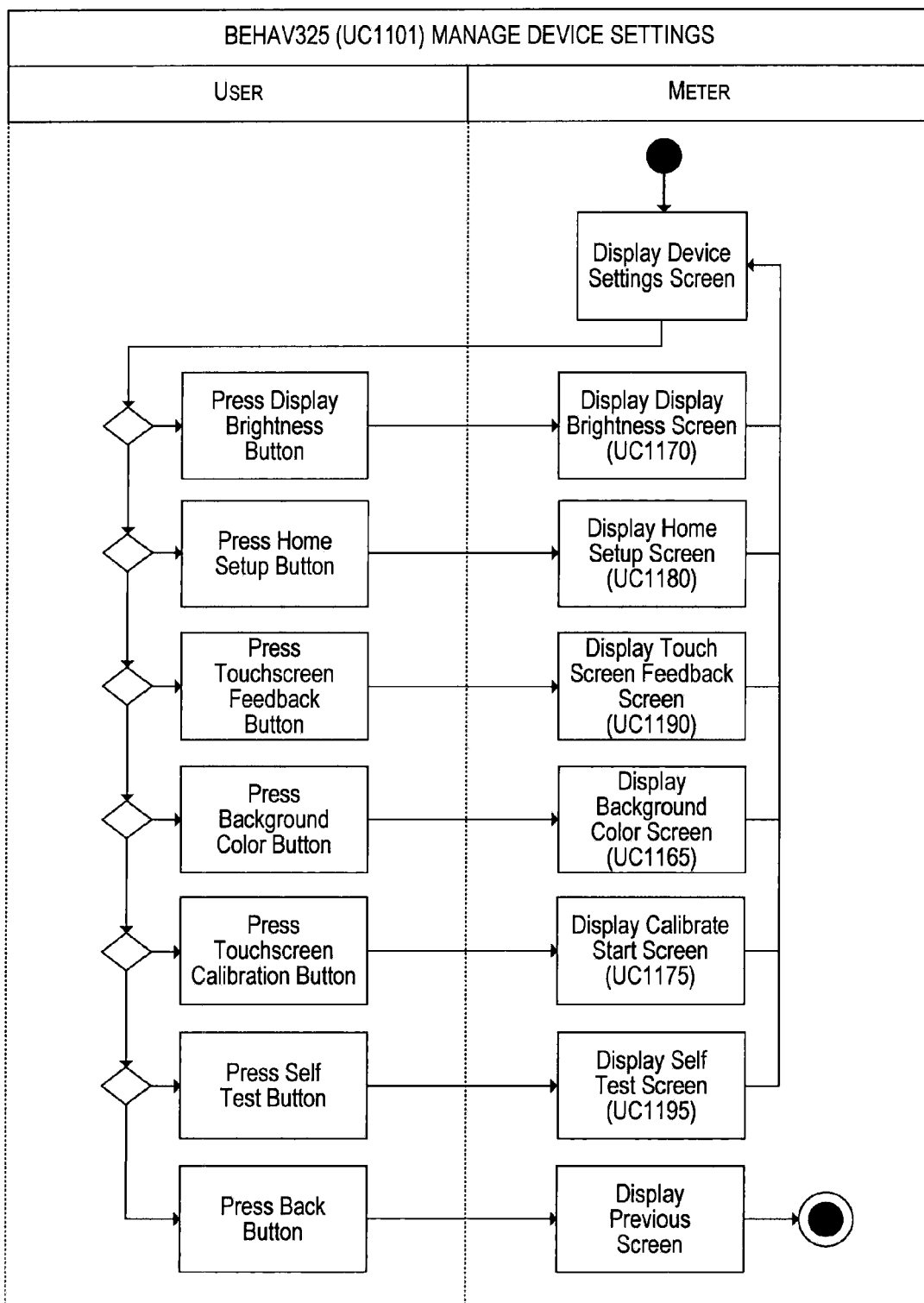
FIG. 20B is an activity diagram illustrating behavioral flow for managing settings for a diabetes manager according to the present teachings.

Referring to FIGS. 20A and 20B, pressing the brightness button 2004 displays a display-brightness screen. Pressing the background-color button 2016 displays a background-color screen. Pressing the meter-function-test button 2020 displays a meter-function-test screen. Pressing the back button 2028 displays the system-settings screen 1400.

Figure 21:
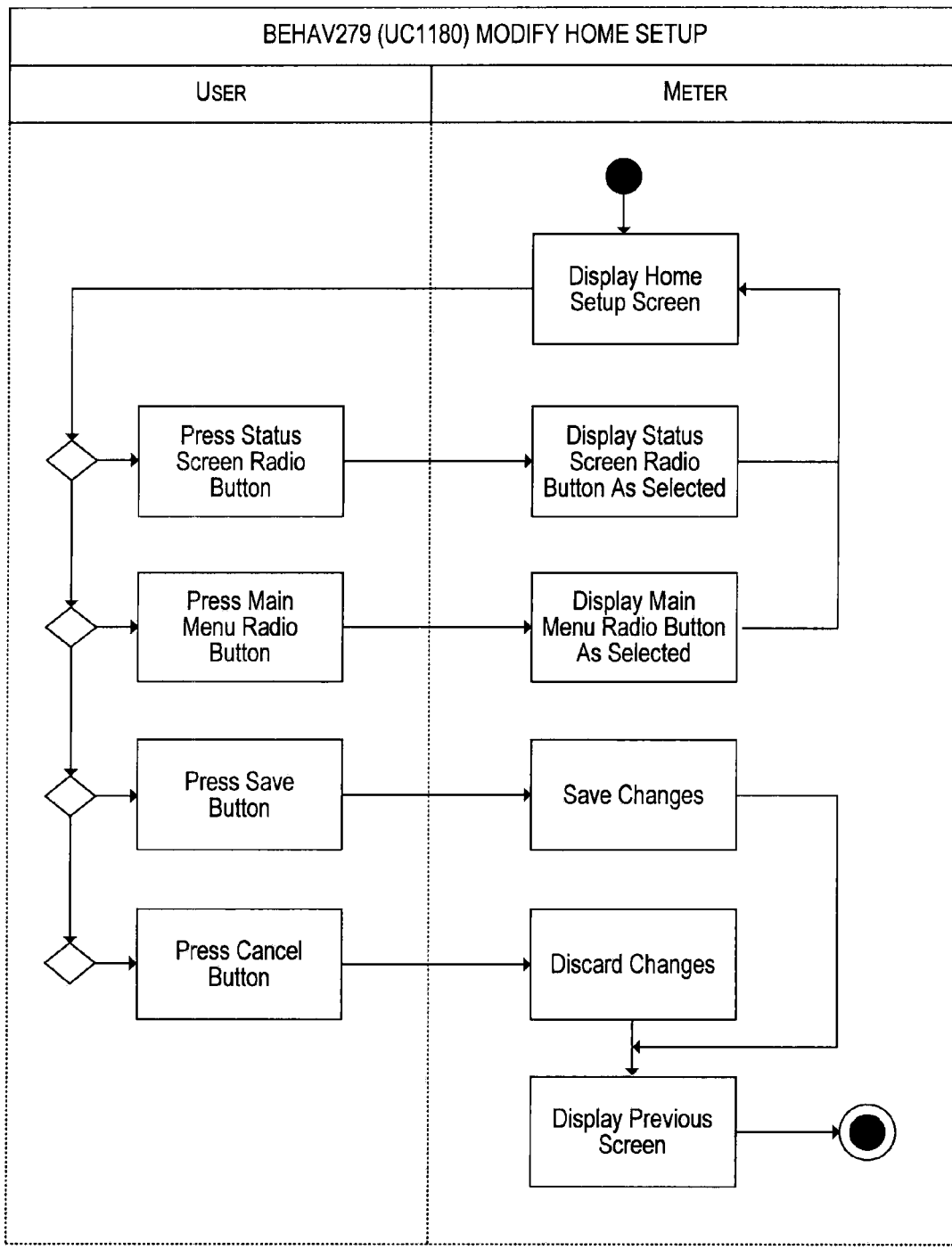
FIG. 21 is an activity diagram illustrating behavioral flow for modifying a home-screen setup for a diabetes manager according to the present teachings.

Referring to FIGS. 20A, 20B, and 21, pressing the home-screen button 2008 displays a home-setup screen. Pressing a main-menu radio button of the home-setup screen highlights the selected radio button and sets the home-screen-configuration value to "Main Menu." Pressing a status-screen radio button of the home-setup screen highlights the selected radio button and sets the home-screen-configuration value to STATUS. Pressing a save button of the home-setup screen saves any changes and returns to the point of entry. Pressing a cancel button of the home-setup screen discards any changes and returns to the point of entry.

FIG. 22 illustrates an exemplary touchscreen-settings screen 2200 of the diabetes manager 104. With reference to FIGS. 20A, 20B, and 22, pressing (or touching) the touchscreen button 2012 of the meter-settings screen 2000 displays the touchscreen-settings screen 2200. The touchscreen-settings screen 2200 may include various buttons (mechanical or touch buttons) that can be activated by touch or stylus or other selector device to display a corresponding screen. The touchscreen-settings screen 2200 may include a tone button 2204, a vibration button 2208, a tone-and-vibration button 2212, a none button 2216, a save button 2220, and a cancel button 2224. Pressing the cancel button 2224 discards any changes and displays the meter-settings screen 2000. Pressing the tone button 2204, the vibration button 2208, the tone-and-vibration button 2212, or the none button 2216 highlights the selected the radio button.

Pressing the save button 2220 while the tone button 2204 or the tone-and-vibration button 2212 is selected sets a BUTTON_SOUND_ENABLED_VAL value to true and displays the meter-settings screen 2000 (or other point of entry). Pressing the save button 2220 while the vibration button 2208 or the tone-and-vibration button 2212 is selected sets a BUTTON_VIBRATE_ENABLED_VAL value to true and displays the meter-settings screen 2000 (or other point of entry). Pressing the cancel button 2224 displays the meter-settings screen 2000 without making any changes. Pressing the save button 2220 while the none button 2216 is selected sets the BUTTON_SOUND_ENABLED_VAL value to false, sets the BUTTON_VIBRATE_ENABLED_VAL value to false, and displays the meter-settings screen 2000 (or other point of entry).

Figure 23:
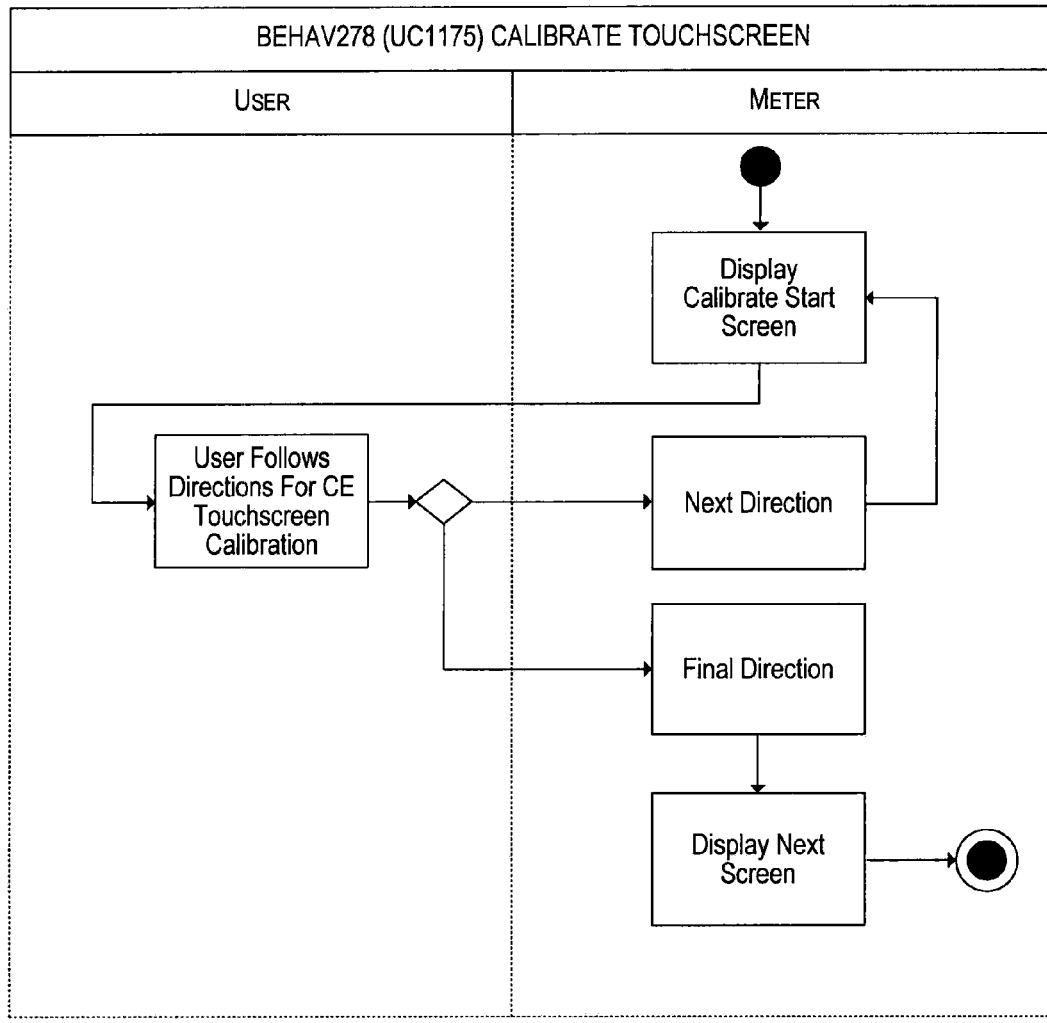
FIG. 23 is an activity diagram illustrating behavioral flow for calibrating a touchscreen of a diabetes manager according to the present teachings.

Referring to FIGS. 20A, 20B, and 23, pressing the screen-calibration button 2024 displays a calibrate-start screen. The diabetes manager 104 shall follow a CE touchscreen calibration routine in display and behavior. When the instructions as specified in the CE touchscreen calibration routine are completed, the diabetes manager 104 shall display the meter-settings screen 2000.

Figure 24A:
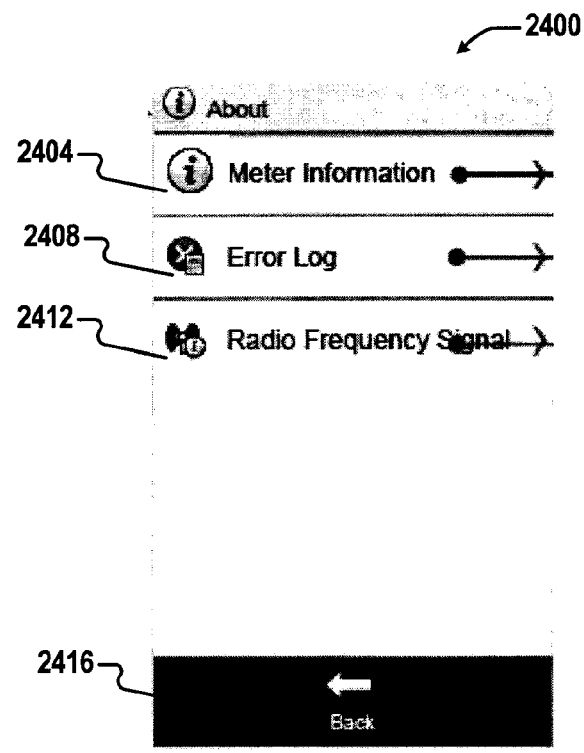
FIG. 24A is an exemplary about screen of a diabetes manager according to the present teachings.

FIG. 24A illustrates an exemplary about screen 2400 of the diabetes manager 104. With reference to FIGS. 14A, 14B, 14C and 24A, pressing (or touching) the about button 1416 of the system-settings screen 1400 displays the about screen 2400. The about screen 2400 may include various buttons (mechanical or touch buttons) that can be activated by touch or stylus or other selector device to display a corresponding screen. The about screen 2400 may include a meter-information button 2404, an error-log button 2408, an RF-signal button 2412, and a back button 2416. Pressing the back button 2416 displays the previous screen.

Figure 25:
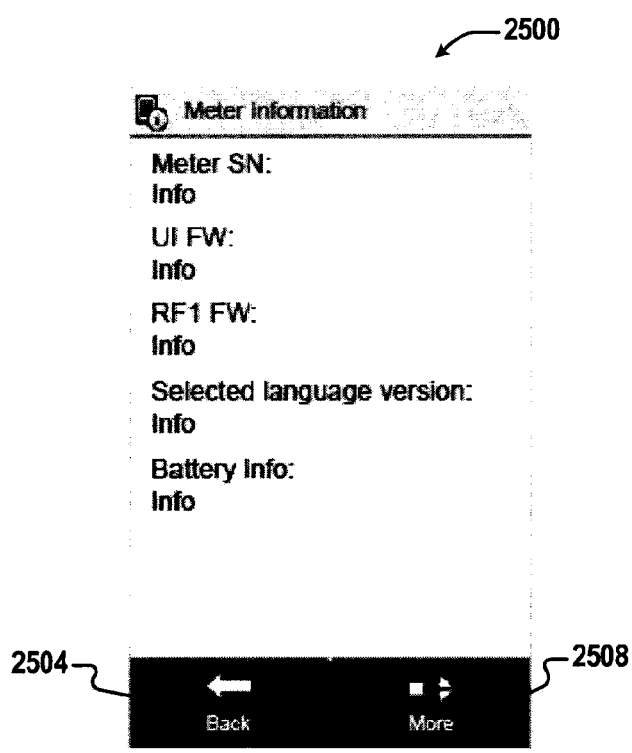
FIG. 25 is an exemplary meter-information screen of a diabetes manager according to the present teachings.

FIG. 25 illustrates an exemplary meter-information screen 2500 of the diabetes manager 104. With reference to FIGS. 24A, 24B, 24C, and 25, pressing (or touching) the meter-information button 2404 of the about screen 2400 displays the meter-information screen 2500. The meter-information screen 2500 may include various pieces of information, such as a meter serial number, a selected language, or battery information. The meter-information screen 2500 may include various buttons (mechanical or touch buttons) that can be activated by touch or stylus or other selector device to display a corresponding screen. The meter-information screen 2500 may include a back button 2504 and a more button 2508.

Pressing the back button 2504 displays the previous screen. Pressing the more button 2508 displays a second meter information screen with additional information. When the meter-information screen 2500 is displayed, and the diabetes manager 104 is upgrading firmware, the diabetes manager 104 shall hide the back button 2504 and the more button 2508.

Figure 24B:
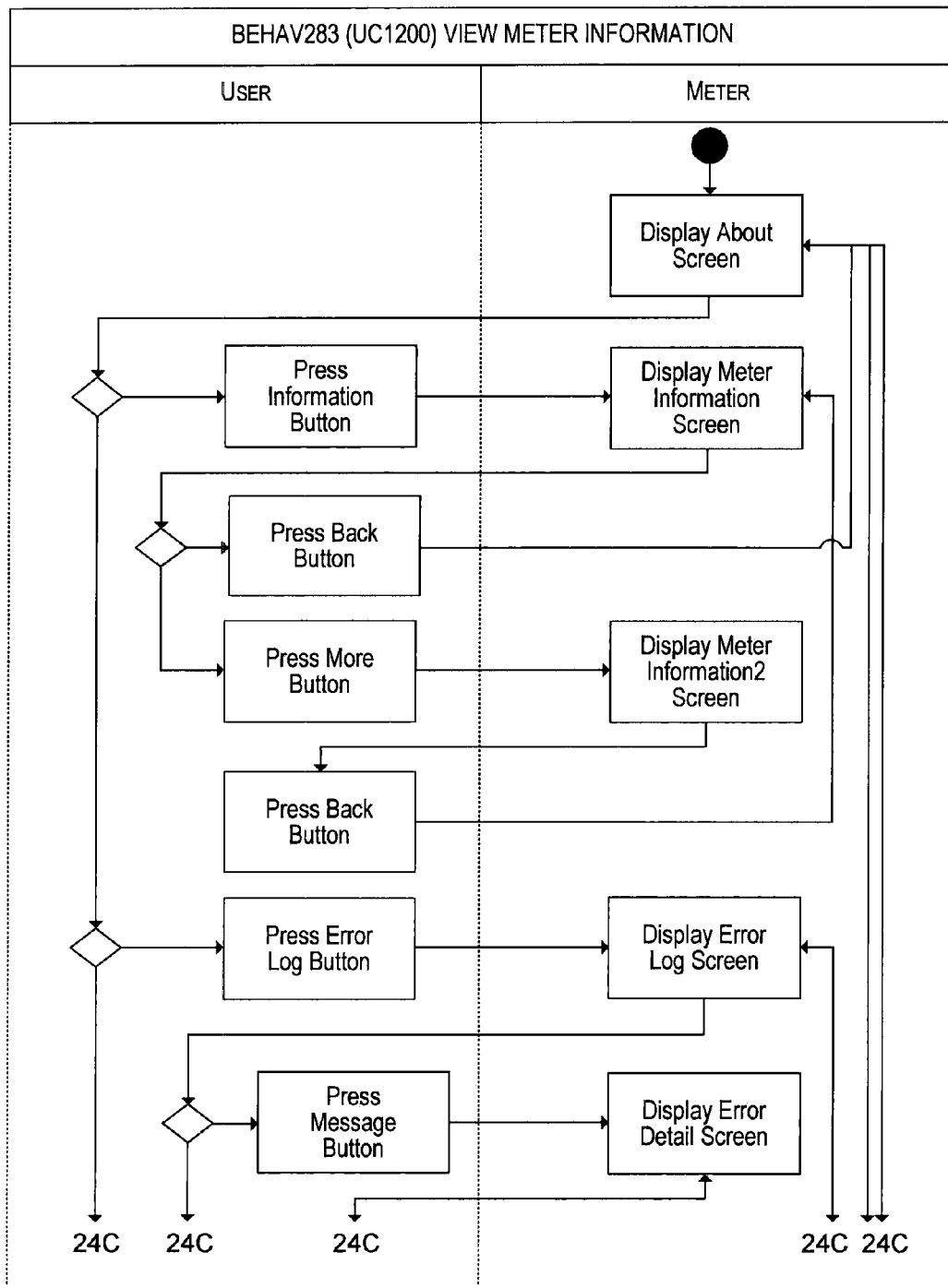
FIGS. 24B and 24C are an activity diagram illustrating behavioral flow for viewing meter information for a diabetes manager according to the present teachings.
Figure 24C:
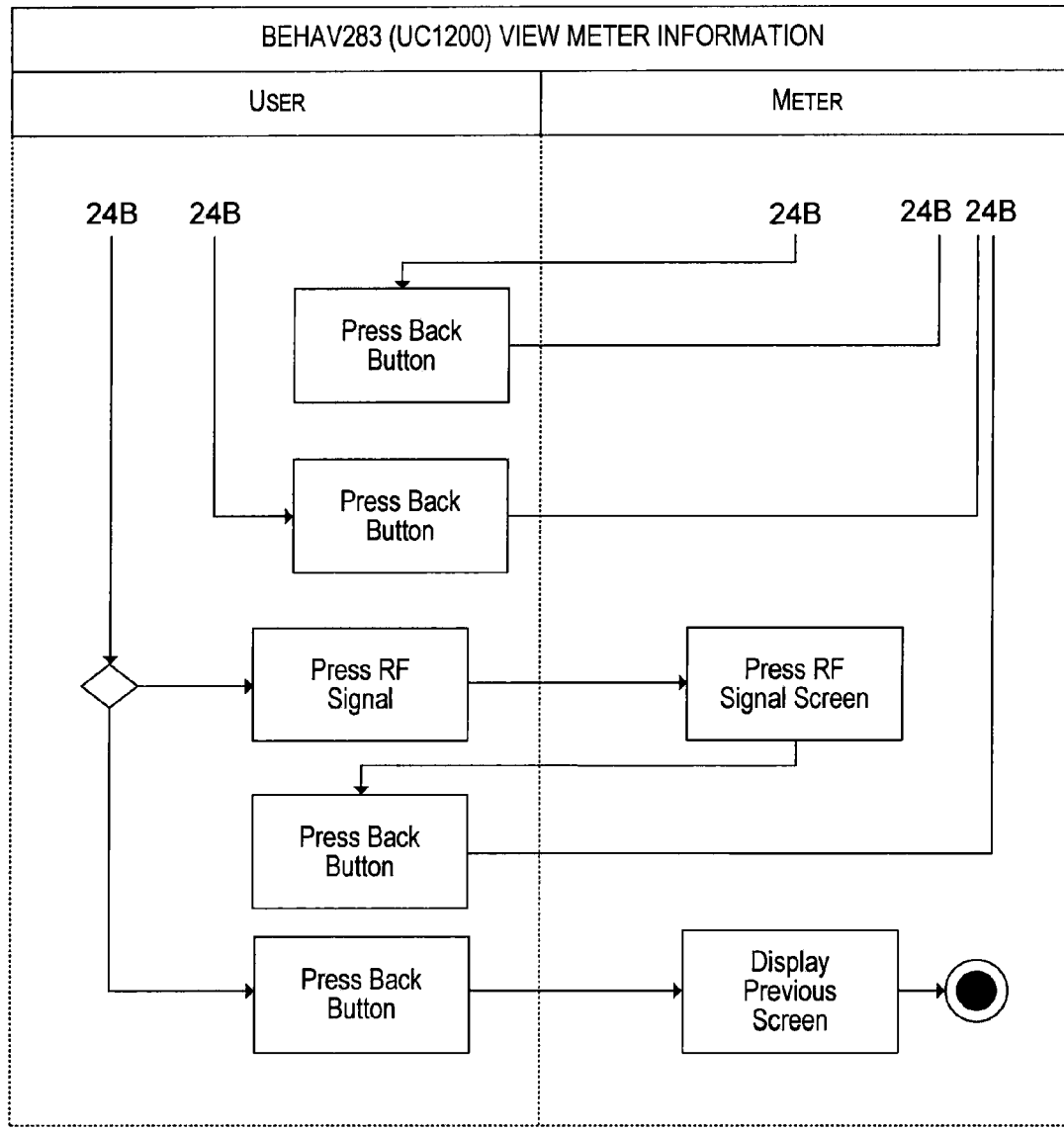

Referring to FIGS. 24B and 24C, pressing the error-log button 2408 of the about screen 2400 displays an error-log screen. Pressing a back button of the error-log screen displays the previous screen. Pressing a message button of the error-log screen displays an error-detail screen. Pressing a back button of the error-detail screen displays the previous screen.

If the meter is not paired to a device, the diabetes manager 104 shall disable the RF-signal button 2412. Pressing the RF-signal button 2412 of the about screen 2400 displays an RF-signal screen. Pressing a back button of the RF-signal screen displays the previous screen.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. For purposes of clarity, the same reference numbers will be used in the drawings to identify similar elements. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method for a handheld diabetes-management device to establish a data connection with a Continua manager, comprising:

receiving, by the diabetes-management device, a request to establish a new data connection with a computing device, where the computing device is physically separated from the diabetes-management device and operates as a manager in accordance with IEEE standard 11073;

determining, by the diabetes-management device, whether the diabetes-management device has an existing data connection with a medical device that is physically separated from the diabetes-management device, the determination being in response to receiving the request to establish a new data connection;

terminating, by the diabetes-management device, the existing data connection with the medical device, the termination being in response to the determination that the diabetes-management device has an existing connection with the medical device; and establishing, by the diabetes-management device, a new data connection with the computing device in accordance with IEEE standard 11073.

2. The method of claim 1 further comprises determining whether the existing data connection is a wired connection with the medical device and, prior to establishing the new data connection with the computing device, prompting a user to disconnect the medical device from the diabetes-management device, thereby terminating the existing data connection with the medical device.

3. The method of claim 2 wherein the existing data connection operates in accordance with Universal Serial Bus standard.

4. The method of claim 1 further comprises detecting, by the diabetes-management device, presence of a wired connection with the computing device and establishing the new data connection via the wired connection with the computing device upon detecting the presence of the wired connection.

5. The method of claim 4 further comprises establishing, by the diabetes-management device, a wireless data connection with the computing device in absence of a wired connection with the computing device.

6. The method of claim 1 wherein establishing a new data connection further comprises sending an associate request by the diabetes-management device to the computing device in accordance with IEEE standard 11073.

7. The method of claim 1 wherein the new data connection operates in accordance with Bluetooth wireless technology standard.

8. A computer-implemented method for a handheld diabetes-management device to establish a data connection with a Continua manager, comprising:
  receiving, by the diabetes-management device, a request to establish a new data connection with a computing device, where the computing device is physically separated from the diabetes-management device and operates as a manager in accordance with IEEE standard 11073;
  determining, by the diabetes-management device, whether the diabetes-management device has an existing data connection with a medical device that is physically separated from the diabetes-management device, the determination being in response to receiving the request to establish a new data connection;
  determining whether the medical device is an insulin pump, the determination being in response to the determination that the diabetes-management device has an existing connection;
  terminating, by the diabetes-management device, the existing data connection with the insulin pump, the termination being in response to the determination that the medical device is an insulin pump; and
  establishing, by the diabetes-management device, a new data connection with the computing device in accordance with IEEE standard 11073.

9. The method of claim 8 further comprises determining whether the existing data connection is a wired connection with the medical device and, prior to establishing the new data connection with the computing device, prompting a user to disconnect the medical device from the diabetes-management device, thereby terminating the existing data connection with the medical device.

10. The method of claim 9 wherein the existing data connection operates in accordance with Universal Serial Bus standard.

11. The method of claim 8 further comprises detecting, by the diabetes-management device, presence of a wired connection with the computing device and establishing the new data connection via the wired connection with the computing device upon detecting the presence of the wired connection.

12. The method of claim 11 further comprises establishing, by the diabetes-management device, a wireless data connection with the computing device in absence of a wired connection with the computing device.

13. The method of claim 11 wherein establishing a new data connection further comprises sending an associate request by the diabetes-management device to the computing device in accordance with IEEE standard 11073.

14. The method of claim 11 wherein the new data connection operates in accordance with Bluetooth wireless technology standard.

15. A handheld diabetes-management device having an automated disconnect feature when establishing a data connection with a Continua manager, comprising:
  a port configured to receive a test strip for blood glucose measurement;
  a blood glucose measurement module cooperatively operable with a test strip inserted in the port for blood glucose measurement;
  a communications module that selectively communicates via a wireless data link with a medical device, the medical device being physically separated from the diabetes manager; and
  a connectivity module configured to receive a request to establish a new data connection with a computing device and operates, in response to the request, to determine whether the diabetes-management device has an existing data connection with the medical device, and further operates, in response to the determination that the diabetes-management device has an existing data connection with the medical device, to terminate the existing data connection with the medical device, where the computing device is physically separated from the diabetes-management device and operates as a manager in accordance with IEEE standard 11073.

16. The handheld diabetes-management device of claim 15 wherein the communications module establishes a new data connection with the computing device following termination of the existing data connection with the medical device.

17. The handheld diabetes-management device of claim 15 wherein the communications module established a new data connection by sending an associate request to the computing device in accordance with IEEE standard 11073.

* * * * *